United States Patent
Takasu et al.

(10) Patent No.: US 10,184,894 B2
(45) Date of Patent: Jan. 22, 2019

(54) CANCER DIAGNOSTIC DEVICE, DIAGNOSTIC SYSTEM, AND DIAGNOSTIC DEVICE

(71) Applicant: Rohm Co., Ltd., Kyoto (JP)

(72) Inventors: Hidemi Takasu, Kyoto (JP); Toshihisa Maeda, Kyoto (JP); Masahide Tanaka, Kyoto (JP); Takuji Maekawa, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 290 days.

(21) Appl. No.: 14/785,902

(22) PCT Filed: Aug. 21, 2014

(86) PCT No.: PCT/JP2014/061186
§ 371 (c)(1),
(2) Date: Oct. 21, 2015

(87) PCT Pub. No.: WO2014/175223
PCT Pub. Date: Oct. 30, 2014

(65) Prior Publication Data
US 2016/0077008 A1    Mar. 17, 2016

(30) Foreign Application Priority Data

Apr. 22, 2013  (JP) ................................ 2013-089515
Apr. 17, 2014  (JP) ................................ 2014-085486

(51) Int. Cl.
*G01N 21/65*       (2006.01)
*H04N 13/344*     (2018.01)
(Continued)

(52) U.S. Cl.
CPC ........... *G01N 21/65* (2013.01); *A61B 1/0005* (2013.01); *A61B 1/00048* (2013.01);
(Continued)

(58) Field of Classification Search
CPC .. G01N 21/65; G01B 27/017; G02B 27/0172; A61B 8/00; A61B 1/00048; A61B 1/0005
See application file for complete search history.

(56) References Cited

U.S. PATENT DOCUMENTS 6,205,354 B1     3/2001  Gellermann et al.
8,901,541 B2 *  12/2014  Nishiyama ........ H01L 27/14609
                                                        257/40
(Continued)

FOREIGN PATENT DOCUMENTS

JP    H05-289001 A    11/1993
JP    07-111970        5/1995
(Continued)

OTHER PUBLICATIONS

Japanese Patent Office, Office Action for Japanese Patent Application No. 2013-089515, dated Mar. 21, 2017, with English translation (11 pages).
(Continued)

Primary Examiner — Behrooz M Senfi
(74) Attorney, Agent, or Firm — Fish & Richardson P.C.

(57) ABSTRACT

A target is irradiated in a time-shared manner with a visible-light-range illumination light source and an infrared laser beam for Raman scattering, and a target image is formed with an image-capturing lens on a CIGS image sensor provided with a visible-light-range filter, a narrow-band infrared filter for Raman-scattered light measurement, and a near-band reference narrow-band infrared filter that does not let Raman-scattered light pass through. In a preliminary measurement, a plurality of normal sections are measured and averaged, and by using the same as a reference, an actual measurement of Raman scattering is performed. In displaying a visible-light image with the CIGS image sensor, superimposed display is performed to specify sections where Raman scattering is detected, and superimposed display
(Continued)

positions are corrected in association with focusing and zooming. The displaying of the visible-light image is continued even during the detection of Raman scattering.

16 Claims, 14 Drawing Sheets

(51) Int. Cl.
| | | |
|---|---|---|
| *A61B 1/00* | (2006.01) | |
| *A61B 1/06* | (2006.01) | |
| *A61B 5/00* | (2006.01) | |
| *G01J 3/02* | (2006.01) | |
| *G01J 3/28* | (2006.01) | |
| *G01J 3/44* | (2006.01) | |
| *G02B 27/01* | (2006.01) | |
| *G06T 7/00* | (2017.01) | |
| *H04N 13/254* | (2018.01) | |
| *H04N 13/257* | (2018.01) | |
| *H04N 13/239* | (2018.01) | |
| *G02B 5/20* | (2006.01) | |
| *H04N 5/225* | (2006.01) | |
| *H04N 5/33* | (2006.01) | |

(52) U.S. Cl.
CPC ...... *A61B 1/00186* (2013.01); *A61B 1/00193* (2013.01); *A61B 1/0638* (2013.01); *A61B 5/0075* (2013.01); *A61B 5/7445* (2013.01); *G01J 3/0208* (2013.01); *G01J 3/0237* (2013.01); *G01J 3/0248* (2013.01); *G01J 3/0264* (2013.01); *G01J 3/2823* (2013.01); *G01J 3/4412* (2013.01); *G02B 27/0172* (2013.01); *G06T 7/0012* (2013.01); *H04N 13/239* (2018.05); *H04N 13/254* (2018.05); *H04N 13/257* (2018.05); *H04N 13/344* (2018.05); *G02B 5/208* (2013.01); *G02B 2027/0134* (2013.01); *G02B 2027/0141* (2013.01); *G02B 2027/0178* (2013.01); *G06T 2207/10048* (2013.01); *G06T 2207/30096* (2013.01); *H04N 5/2256* (2013.01); *H04N 5/332* (2013.01)

(56) References Cited

U.S. PATENT DOCUMENTS

| | | | |
|---|---|---|---|
| 2006/0001740 A1 | 1/2006 | Fujie et al. | |
| 2006/0239673 A1 | 10/2006 | Mansbridge | |
| 2007/0046778 A1* | 3/2007 | Ishihara | A61B 1/00009 348/68 |
| 2011/0058716 A1 | 3/2011 | Okawa et al. | |
| 2011/0134293 A1* | 6/2011 | Tanaka | G02B 7/34 348/280 |
| 2012/0086095 A1 | 4/2012 | Nishiyama et al. | |
| 2012/0148164 A1* | 6/2012 | Suk | G06K 9/46 382/201 |
| 2013/0236923 A1* | 9/2013 | Popescu | G01N 21/47 435/29 |
| 2013/0267855 A1* | 10/2013 | Tsubota | A61B 5/0075 600/473 |
| 2014/0055563 A1 | 2/2014 | Jessop | |
| 2014/0111628 A1 | 4/2014 | Yoshino et al. | |
| 2014/0210972 A1* | 7/2014 | On | G02B 7/36 348/65 |
| 2014/0218479 A1 | 8/2014 | Nishimura | |
| 2015/0182126 A1* | 7/2015 | Fukutani | A61B 5/0095 600/407 |
| 2015/0335248 A1 | 11/2015 | Huang et al. | |
| 2017/0079512 A1 | 3/2017 | Jessop | |

FOREIGN PATENT DOCUMENTS

| | | | |
|---|---|---|---|
| JP | H08-313828 A | 11/1996 | |
| JP | H9-098985 A | 4/1997 | |
| JP | 2001-091892 A | 4/2001 | |
| JP | 2002-005835 A | 1/2002 | |
| JP | 2003-507088 A | 2/2003 | |
| JP | 2005-103048 A | 4/2005 | |
| JP | 2006-300611 | 11/2006 | |
| JP | 2010-227200 A | 10/2010 | |
| JP | WO 2010116974 A1 * | 10/2010 | ....... H01L 27/14609 |
| JP | 2012-125455 A | 7/2012 | |
| JP | 2013-090035 A | 5/2013 | |
| JP | 2013-223635 A | 10/2013 | |
| JP | 2013-545557 A | 12/2013 | |
| WO | WO2009/148044 A1 | 12/2009 | |
| WO | 2010/024397 A1 | 3/2010 | |
| WO | 2010/116974 A1 | 10/2010 | |
| WO | 2013/027460 | 2/2013 | |
| WO | 2014/007759 A1 | 1/2014 | |

OTHER PUBLICATIONS

Japanese Patent Office, International Search Report for PCT/JP2014/061186 dated Jul. 15, 2014 (with English translation).

Japanese Patent Office; Japanese Office Action dated Oct. 24, 2017 in corresponding Japanese Patent Application No. 2013-089515 (with English-language translation).

Japanese Patent Office; Office Action mailed in corresponding Japanese Patent Application No. 2014-085486 dated Apr. 10, 2018 (with English translation).

Gomi Y., et al., "A Consideration of Using Head Mounted Display on Endoscopic Surgery," Information Processing Society Japan, pp. 78-81, 2008 (with abstract/partial English translation).

Japanese Patent Office; Office Action dated Oct. 23, 2018 in Japanese Patent Application No. 2014-085486 (with English Translation).

K.Muramatsu et al., "Design and Implementation of a Communication Support System with Wearable Devices for Dentistry," Information Processing Society of Japan, 49th vol., No. 1 , Jan. 15, 2008 (with English Abstract).

\* cited by examiner

FIG.5A
FIG.5B
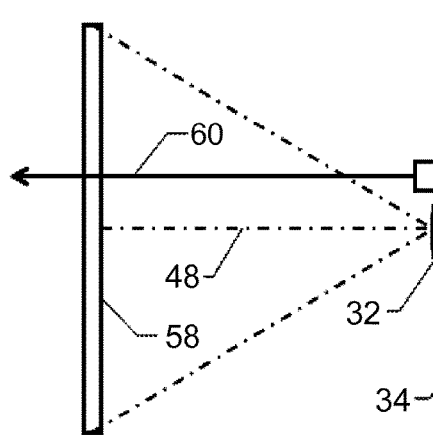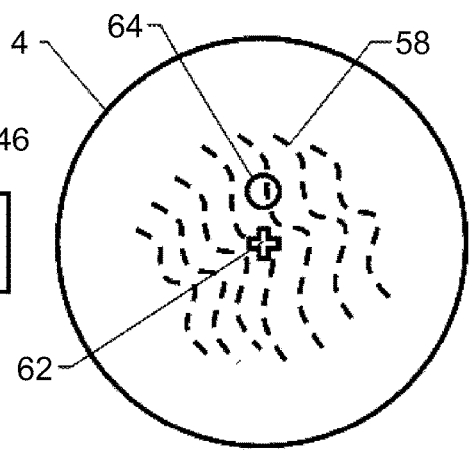
FIG.5C
FIG.5D
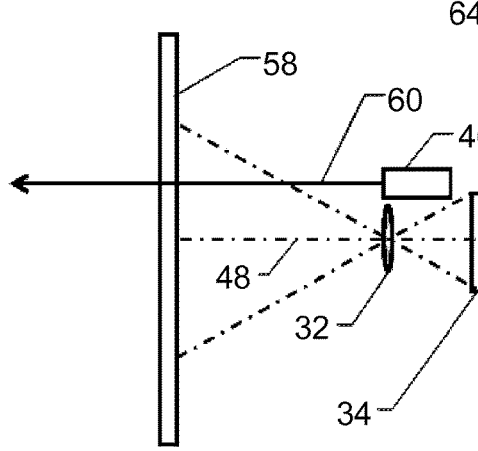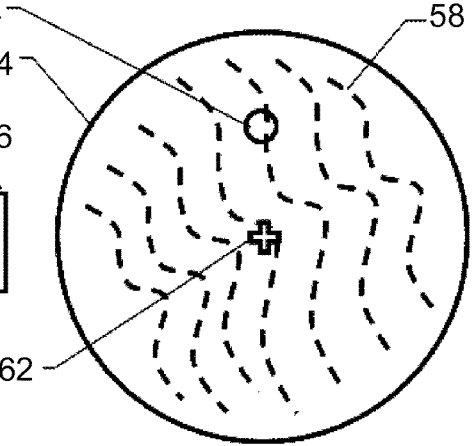
FIG.5E
FIG.5F
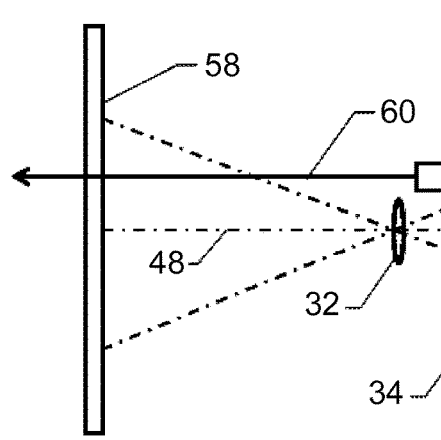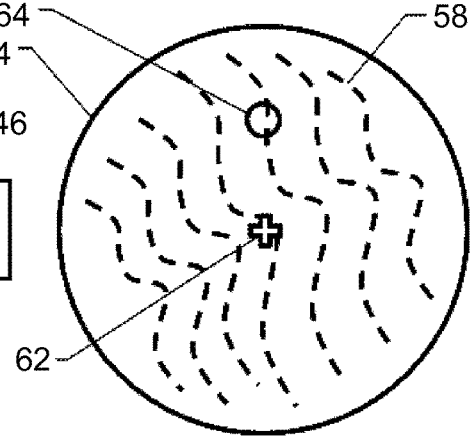

CANCER DIAGNOSTIC DEVICE, DIAGNOSTIC SYSTEM, AND DIAGNOSTIC DEVICE

TECHNICAL FIELD

The present invention relates to a diagnostic system, a diagnostic device, and a display device, and more specifically to a cancer diagnostic device.

BACKGROUND ART

Various proposals have been made as to diagnostic systems and diagnostic devices. For instance, Japanese translation Publication of PCT International application No. 2003-507088 (Patent Document 1) proposes an evaluation method in cancer diagnosis, in which an tissue to be measured is irradiated with a laser beam from a light source, Raman-scattered light is separated from Rayleigh scattered light by spectrum separation, and a substantial difference between intensity of Raman-scattered light from a biological tissue that may be a malignant tumor and intensity of Raman-scattered light from a neighboring normal biological tissue is evaluated as presence or risk of illness. In addition, JP-A-2002-5835 (Patent Document 2) proposes a method of discernment between a normal tissue and a cancer tissue using Raman spectrum, in which pulse-like near infrared light having a wavelength of 1064 nm from a Nd:YAG laser light source 10 is used as excitation light for irradiating a specimen, and Raman-scattered light split by a spectrometer and detected by a photodetector 31 is counted by a coincidence counting circuit, based on an excitation light detection signal from a photo diode 16 for detecting the excitation light, in synchronization with the excitation light, and hence intensity of background light in the Raman spectrum is reduced.

PRIOR ART DOCUMENTS

Patent Documents

Patent Document 1: Japanese translation Publication of PCT International application No. 2003-507088
Patent Document 2: JP-A-2002-5835

DISCLOSURE OF THE INVENTION

Problem to be Solved by the Invention

However, there are many issues to be considered about a diagnostic system, a diagnostic device, a display device, and a cancer diagnostic device.

In view of the above discussion, it is an object of the present invention to provide a diagnostic system, a diagnostic device, a display device, and a cancer diagnostic device, which are easier to use.

Means for Solving the Problem

In order to solve the above-mentioned problem, the present invention provides a cancer diagnostic device including a CIGS image sensor provided with a visible-light-range filter and a Raman scattering detection filter. Specifically, the Raman scattering detection filter includes a measurement infrared filter that selectively transmits Raman-scattered light and a reference infrared filter that selectively transmits near-band infrared light without Raman-scattered light.

According to another specific feature, the cancer diagnostic device of the present invention includes a visible-light-range illumination light source and a Raman scattering light source, and the CIGS image sensor performs capturing of a visible-light image and detection of Raman scattering on the basis of the visible-light-range illumination light source and the Raman scattering light source, respectively.

According to still another specific feature, the cancer diagnostic device includes a storing portion arranged to store an output of the CIGS image sensor with the Raman scattering detection filter as a reference value. More specifically, the storing portion stores an average value of a plurality of measured values by the CIGS image sensor with the Raman scattering detection filter as the reference value.

According to still another specific feature, capturing of a visible-light image by the CIGS image sensor and detection of Raman scattering are performed in a time-shared manner, a display portion arranged to display the visible-light image is provided, and displaying of the visible-light image in the display portion is continued even during the detection of Raman scattering.

According to still another specific feature, in displaying of the visible-light image by the CIGS image sensor, superimposed display is performed to specify sections where Raman scattering is detected. More specifically, an image-capturing lens arranged to form an image of a measurement target on the CIGS image sensor is provided, and the superimposed display to specify the sections where Raman scattering is detected is changed in accordance with focus adjustment or zooming of the image-capturing lens.

According to another specific feature, the present invention is embodied as a diagnostic system including a cancer diagnostic device and a plurality of wearable display devices arranged to perform short range wireless communication with the cancer diagnostic device so as to display received diagnosis information.

According to another feature of the present invention, a diagnostic device there is provided, which includes an image-capturing lens, can perform capturing of a visible-light image and diagnosis measurement, performs superimposed display to specify a target section of the diagnosis measurement in displaying of the visible-light image, and changes a superimposed display position in accordance with adjustment of the image-capturing lens.

According to another feature of the present invention, a diagnostic system is provided, which includes a diagnosis information acquiring portion arranged to acquire the diagnosis information, and a plurality of wearable display devices arranged to perform short range wireless communication with the diagnosis information acquiring portion so as to display received diagnosis information.

According to a specific feature of the present invention described above, the diagnosis information acquiring portion provides at least one of the plurality of wearable display devices with diagnosis information partially restricted from full information provided to other wearable display devices.

According to another specific feature, at least one of the plurality of wearable display devices is worn by an examinee. In addition, according to another specific feature, the plurality of wearable display devices are worn by a plurality of examining staff members so that the diagnosis information is shared.

According to another specific feature, the plurality of wearable display devices include telephoning means for the plurality of examining staff members to telephone with each other. Further, according to a specific feature, at least one of the plurality of wearable display devices is worn by the examinee, and the wearable display device worn by the examinee is provided with mute means arranged to prevent the voice of the telephoning means from being transmitted.

According to another specific feature, the diagnosis information acquiring portion acquires 3D image information, and the plurality of wearable display devices include a 3D image display portion. More specifically, a distance between a pair of optical axes for the diagnosis information acquiring portion to acquire 3D image information is different from a distance between eyes in the plurality of wearable display devices, and means for adjusting between them are provided.

According to another specific feature, the diagnosis information acquiring portion acquires a pair of images as the 3D image information, and the diagnostic system includes means for determining barycenters of the pair of images and analysis means arranged to analyze a difference between the barycenters of the pair of images.

Effects of the Invention

As described above, according to the present invention, a diagnostic system, a diagnostic device, a display device, and a cancer diagnostic device, which are easier to use can be provided.

BRIEF DESCRIPTION OF THE DRAWINGS

FIG. 5A is a cross-sectional view of an image capturing optical system of Example 1 (at a wide end of zoom).

FIG. 5B is a monitor display diagram in a state of FIG. 5A.

FIG. 5C is a cross-sectional view of the image capturing optical system of Example 1 when approaching a target at the wide end FIG. 5D is a monitor display diagram in a state of FIG. 5C.

FIG. 5E is a cross-sectional view of the image capturing optical system of Example 1 when zooming in while an imaging distance of FIG. 5A is maintained FIG. 5F is a monitor display diagram in a state of FIG. 5E.

BEST MODE FOR CARRYING OUT THE INVENTION

Example 1

Figure 1:
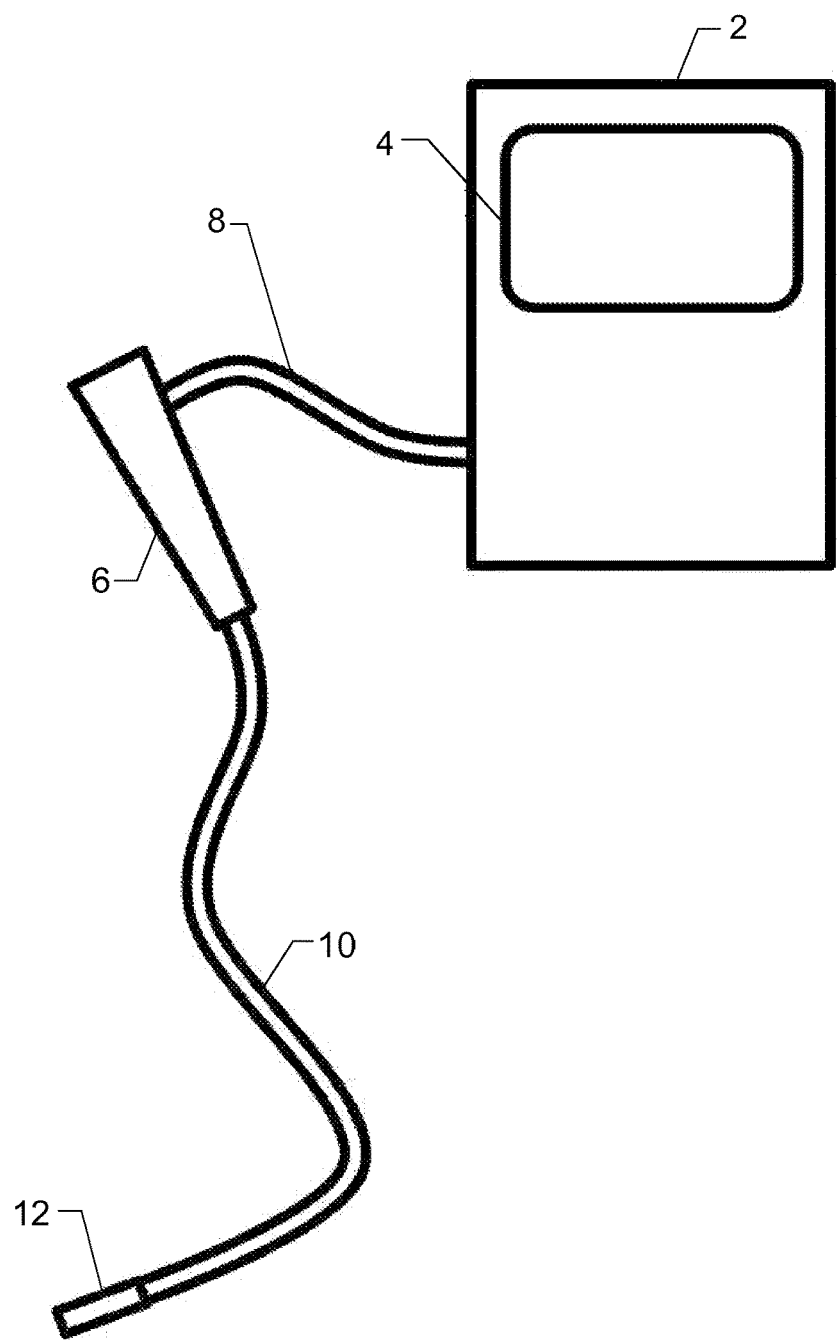
FIG. 1 is a schematic diagram showing a general structure of Example 1 of an endoscope according to the present invention (Example 1).

FIG. 1 is a schematic diagram showing a general structure of Example 1 of an endoscope according to an embodiment of the present invention. The endoscope of Example 1 is controlled by a controlling unit 2, and the controlling unit 2 is equipped with a monitor 4 for displaying an observed image and the like. An operation unit 6 is connected to the controlling unit 2 with a connection cable 8, and the connection cable 8 includes an optical fiber for transmitting light from a light source and signal wires for transmitting electric signals, and the like. The operation unit 6 is held by a doctor, and an insertion portion 10 extends from the operation unit 6 so as to be inserted into a stomach or the like. A distal end of the insertion portion 10 is a tip portion 12 in which an image capturing optical system and an illumination optical system are disposed. The endoscope of Example 1 has a normal function of observing an image of a stomach or the like and another function of irradiating the stomach or the like with a laser beam so as to detect Raman scattering thereof for discerning between a normal tissue and a cancer tissue.

Figure 2:
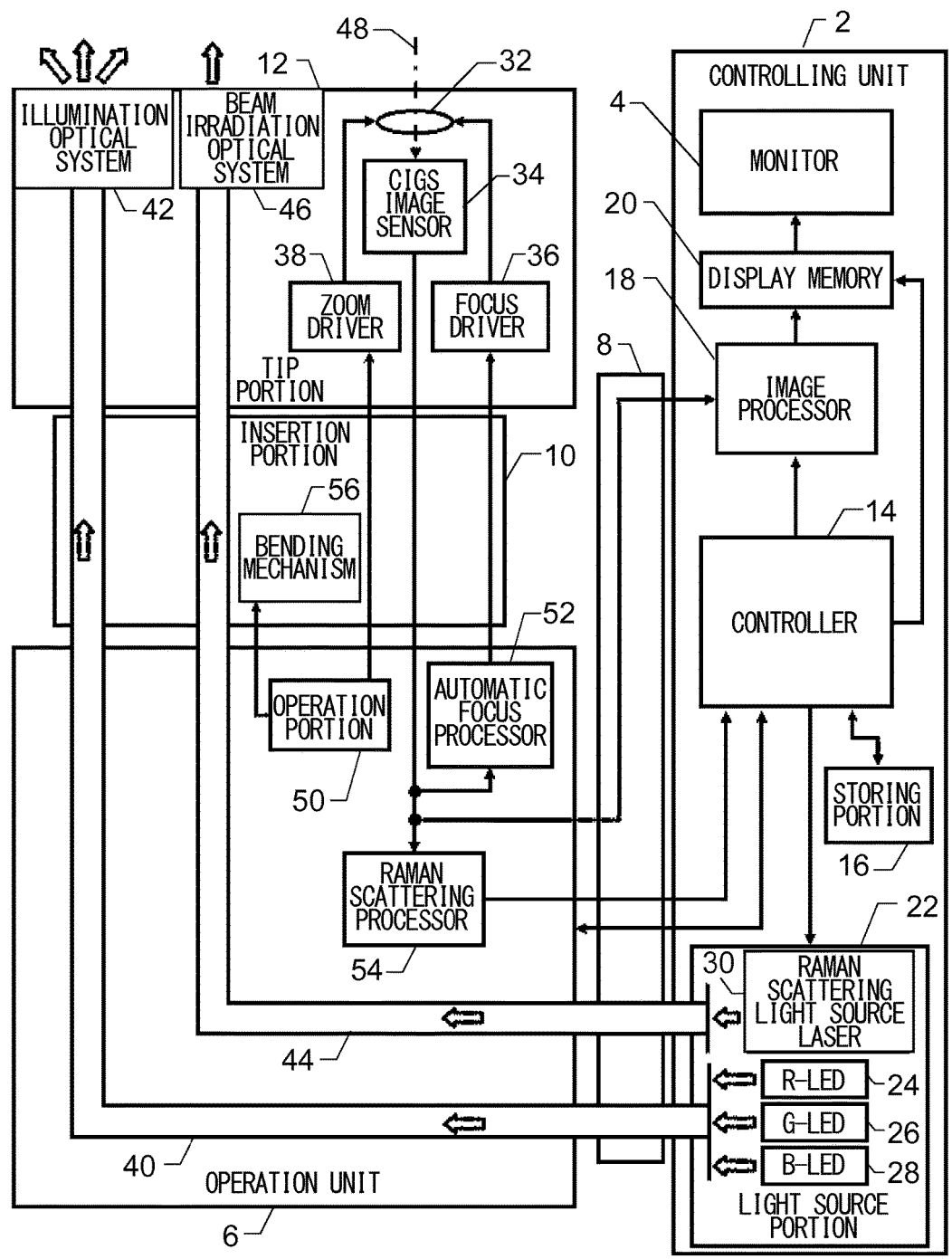
FIG. 2 is a block diagram of a general structure of the endoscope of Example 1 shown in FIG. 1.

FIG. 2 is a block diagram of a general structure of the endoscope of Example 1 shown in FIG. 1, and a portion corresponding to that in FIG. 1 is denoted by the same numeral. The controlling unit 2 is provided with a controller 14 arranged to generally control the entire of the endoscope. A storing portion 16 stores a control program necessary for operation of the controller 14 and stores measured data in an accumulating manner. In addition, the storing portion 16 temporarily stores data related to control.

An image processor 18 processes an endoscope image captured by the tip portion 12 and updates image data for display in a display memory 20 when a new color image is obtained. Then the monitor 4 displays the image based on the image data for display in the display memory 20. The image processor 18 further performs superimposed display of a position irradiated with the light source beam for detecting Raman scattering on the endoscope image, so as to display a position of the light source beam in the endoscope image. As described later, capturing of the endoscope image and detection of Raman scattering are performed in a time-shared manner, but the display memory 20 holds the latest endoscope image even during a time slot in which no endoscope image is captured for detecting Raman scattering, so that the monitor 4 continues displaying.

The controlling unit 2 is further provided with a light source portion 22, which is controlled by the controller 14 to sequentially emit light beams from a red color LED 24, a green color LED 26 and a blue color LED 28 in a time slot for capturing the endoscope image. The light source portion 22 is further provided with a Raman scattering light source laser 30 generating infrared light (e.g., 1056 nm), which is controlled by the controller 14 to emit light in a time slot for detecting Raman scattering.

The tip portion 12 is provided with an image-capturing lens 32 capable of adjusting focus and zooming, and a CIGS image sensor 34 captures a visible-light image with the image-capturing lens 32. The CIGS image sensor 34 is a photoelectronic sensor using a polycrystalline CIGS thin film made of copper, indium, gallium, and selenide. The composition thereof is controlled so that the bandgap is changed, and hence the absorption wavelength range is controlled to have a wide sensitivity range from approximately 400 nm to approximately 1300 nm. Thus, the CIGS image sensor 34 can capture a visible-light image by outputting images at timings of sequential light emission of the red color LED 24, the green color LED 26, and the blue color LED 28, and also functions as a sensor for detecting Raman-scattered light of 1258 nm with respect to light from the light source of 1056 nm as described later.

The image-capturing lens 32 is automatically focus-adjusted by a focus driver 36 that works on the basis of an automatic focus signal and manually zoomed by a zoom driver 38 that works on the basis of a manual operation signal. The visible illumination light emitted sequentially from the red color LED 24, the green color LED 26, and the blue color LED 28 are led in an illumination optical fiber 40 so as to illuminate a range of filed of view covered by the widest field angle of the image-capturing lens 32 via an illumination optical system 42. In addition, the laser beam emitted from the Raman scattering light source laser 30 is guided in a laser optical fiber 44 so as to irradiate the light source beam via a beam irradiation optical system 46 in parallel to an optical axis 48 of the image-capturing lens 32.

An operation portion 50 is disposed in the operation unit 6 through which the illumination optical fiber 40 and the laser optical fiber 44 pass, and this operation portion 50 is manually operated so that a zoom manual operation signal is transmitted to the zoom driver 38. In addition, an automatic focus processor 52 of the operation unit 6 detects and processes contrast of an image output of the CIGS image sensor 34 on the basis of the image output when the green color LED 26 is emitted, and transmits an automatic focus control signal for driving the image-capturing lens 32 to the focus driver 36 so that the contrast is increased on the basis of control by the controller 14. Further, a Raman scattering processor 54 of the operation unit 6 processes the output of the CIGS image sensor 34 at timing when the Raman scattering light source laser 30 emits the laser beam, and sends the processed result to the controller 14. Further, outputting from the CIGS image sensor 34 at timings when the red color LED 24, the green color LED 26, and the blue color LED 28 sequentially emit light is also performed via the operation unit 6.

Further, as described above, connection of the optical fibers 40 and 44, and connection of the signal wires for transmitting the electric signals between the operation unit 6 and the controlling unit 2 are performed via the connection cable 8. In addition, connection of the optical fibers 40 and 44, and connection of the signal wires for transmitting the electric signals between the operation unit 6 and the tip portion 12 are performed via the insertion portion 10. In addition, a bending mechanism 56 for arbitrarily changing an orientation of the tip portion 12 relative to the insertion portion 10 is disposed near the end of the insertion portion 10, and a bending control signal based on a manual operation with the operation portion 50 of the operation unit 6 is transmitted.

Figure 3:
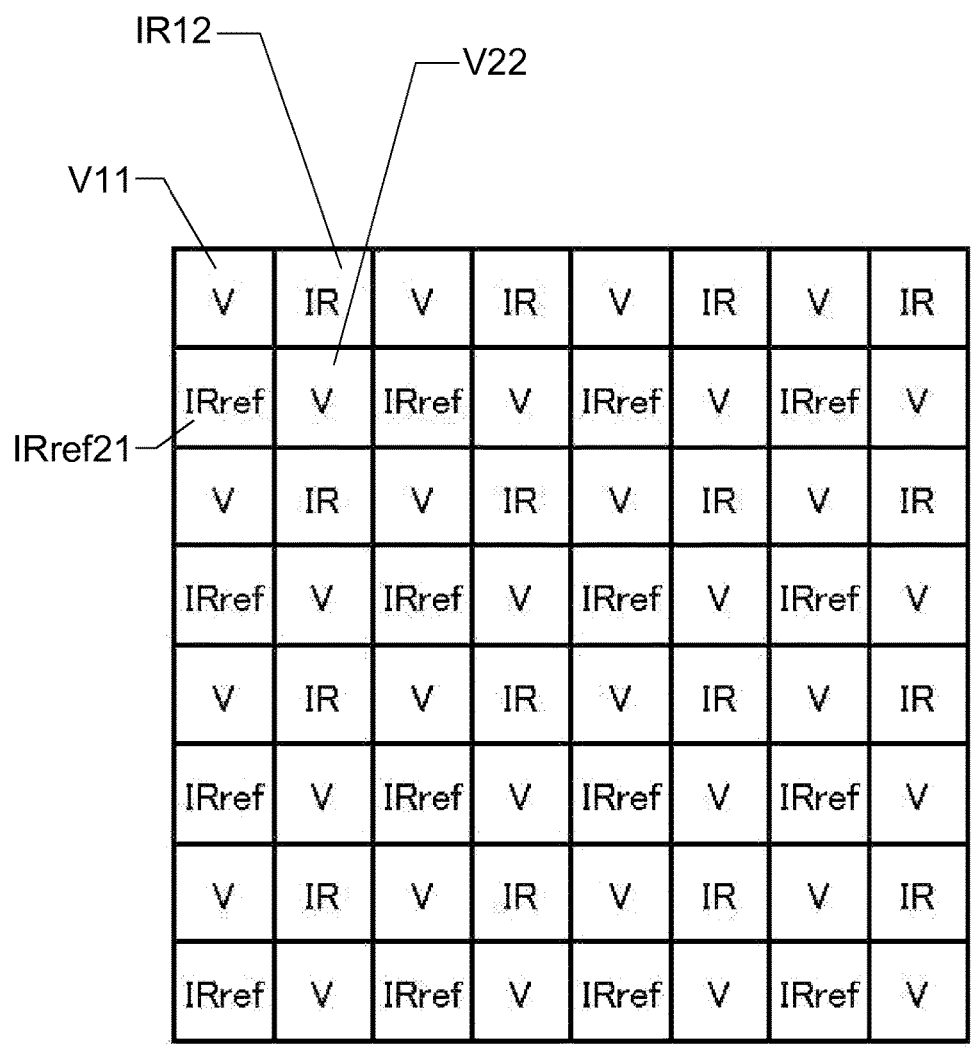
FIG. 3 is a color filter arrangement diagram of a CIGS image sensor of Example 1 shown in FIG. 2.

FIG. 3 is a color filter arrangement diagram of the CIGS image sensor 34 of Example 1 shown in FIG. 2. In the CIGS image sensor 34, there are arranged visible light range filters V11 and V22 for transmitting visible light while cutting infrared light, a narrow-band measurement infrared filter IR12 having a half width of ±4 nm with respect to 1258 nm for selectively transmitting the Raman-scattered light, and a narrow-band reference infrared filter IRref21 having a half width of ±4 nm with respect to 1271 nm for selectively transmitting the near-band infrared light without Raman-scattered light, as shown in the figure, and a set of these filters is repeated in the arrangement. The CIGS image sensor 34 of the present invention has a wide spectral sensitivity range from visible light range to infrared light range as described above, and hence the single sensor is provided with the color filters for visible light and the filter for infrared light, so that detection of a visible-light image and measurement of Raman-scattered light can be simultaneously performed.

As described above, using the narrow-band measurement infrared filter IR12 and reference infrared filter IRref21, the Rayleigh scattered light based on the light from the light source of the Raman scattering light source laser 30 of 1056 nm can be removed. Further, when the Raman-scattered light is measured, outputs of all pixels on which the measurement infrared filters IR12 are disposed are added, outputs of all pixels on which the reference infrared filters IRref21 are disposed are added, and a difference between the added values is calculated so that intensity of the Raman-scattered light at 1258 nm can be detected.

Further, when the visible-light image is formed, as for an image with the measurement infrared filter IR12 and the reference infrared filter IRref21, interpolation is performed by using data of surrounding pixels with the visible light range filter so that the pixel signal is obtained. The interpolation is performed for each of the red color image, the green color image, and the blue color image at timings when the red color LED 24, the green color LED 26, and the blue color LED 28 sequentially emit light.

Figure 4:
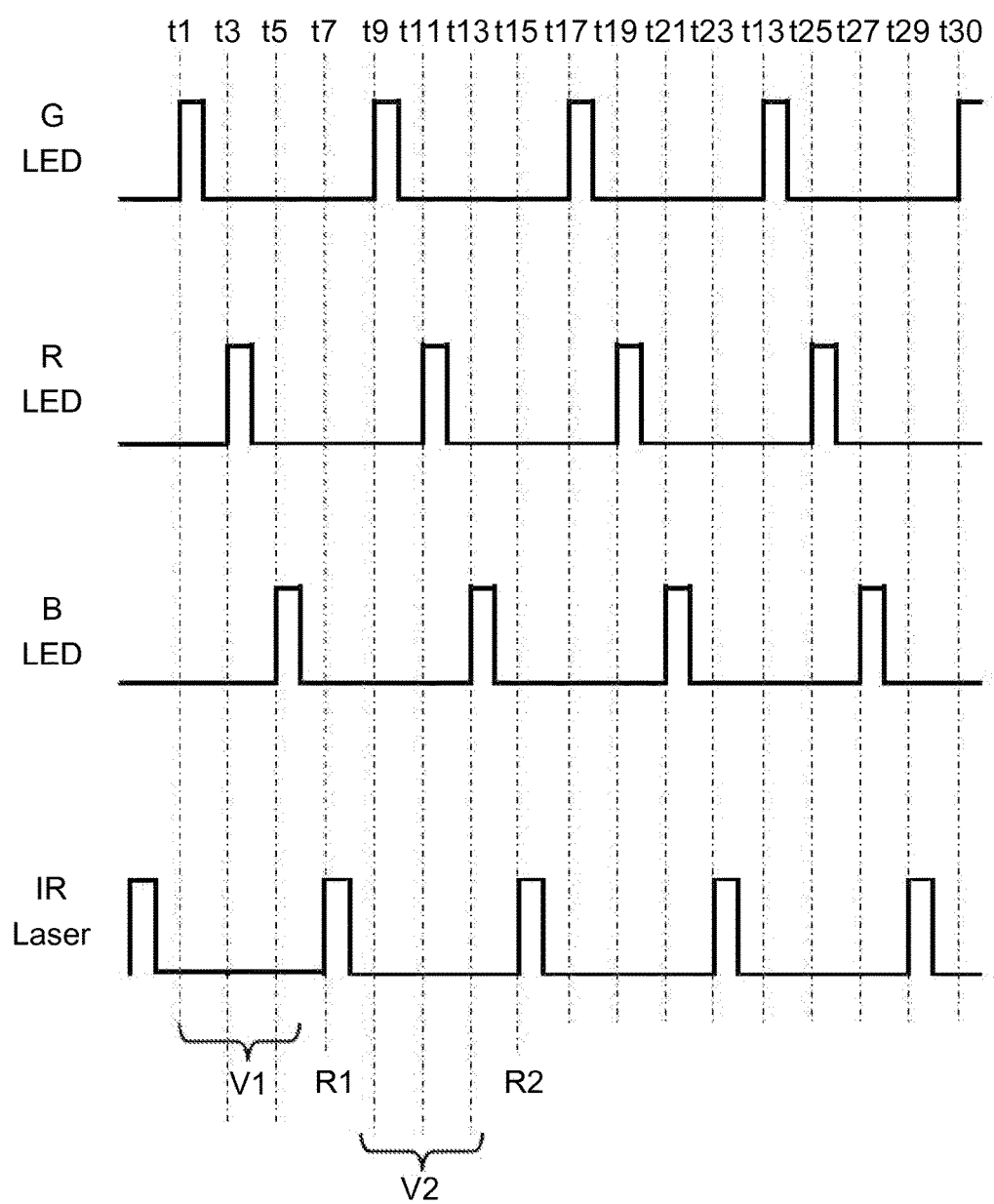
FIG. 4 is a timing chart showing a relationship among light emissions from red color, green color, and blue color LEDs of Example 1 shown in FIG. 2 and laser beam emission from a Raman scattering light source laser 30.

FIG. 4 is a timing chart showing a relationship among light emissions of the red color LED 24, the green color LED 26, and the blue color LED 28 of Example 1 shown in FIG. 2 and emission timing of the laser beam from the Raman scattering light source laser 30 to the measurement target. As shown in FIG. 4, a visible light color image of one frame denoted by V1 is formed of the green color image based on the light emission from the green color LED 26 starting at t1, the red color image based on the light emission from the red color LED 24 starting at t3, and the blue color image based on the light emission from the blue color LED 28 starting at t5. Strictly speaking, because there is a time difference between light emission timings of colors, the images of the colors are not images at the same time. However, because the time difference is very small, there is no problem in capturing the color images in a time-shared manner unless the subject is moving at high speed. In the same manner, a visible light color image of one frame denoted by V2 is formed of the green color image based on the light emission from the green color LED 26 starting at t9, the red color image based on the light emission from the red color LED 24 starting at t11, and the blue color image based on the light emission from the blue color LED 28 starting at t13. After that, in the same manner, a color image of one frame is formed, each color moving image can also be recorded as still images, which can be connected and recorded as a color moving image. Note that the color processing is performed by the image processor 18 shown in FIG. 2.

On the other hand, concerning measurement of the Raman scattering, as shown in FIG. 4, outputs of all pixels corresponding to the measurement infrared filter IR12 are added on the basis of irradiation of the measurement target with the laser beam emitted from the Raman scattering light source laser 30 starting at t7, outputs of all images corresponding to the reference infrared filter IRref21 at the same timing are added, and a difference between the added values is calculated so that Raman scattering intensity R1 is determined. In the same manner, outputs of all pixels corresponding to the measurement infrared filter IR12 are added on the basis of the laser beam emission starting at t15 are added, outputs of all images corresponding to the reference infrared filter IRref21 at the same timing are added, and a difference between the added values is calculated so that Raman scattering intensity R2 is determined. After that, in the same manner, the Raman scattering intensity can be continuously measured in parallel to the capturing of a visible-light image, in a time-shared manner. Accordingly, Raman scattering intensity can be measured for a laser-irradiated position superimposed and displayed on the visible-light image while measuring the target with the visible-light image. Further, the measurement can be continued while changing a measurement position by observing the visible light.

FIG. 5A to 5F show cross-sectional views and monitor display diagrams of an image capturing optical system of the endoscope of Example 1 shown in FIG. 2, for explaining a display of a beam position on a monitor display. A portion corresponding to that in FIG. 2 is denoted by the same numeral, and description thereof is omitted unless it is necessary. FIG. 5A schematically schematically shows a cross section of the image capturing optical system of the endoscope at a longest imaging distance at a wide end (widest side) of the zoom. An image of a target 58 such as a stomach wall to be imaged and measured is formed on the CIGS image sensor 34, and a light source beam 60 irradiates the target 58 from the beam irradiation optical system 46 in parallel to the optical axis 48 of the image-capturing lens 32.

FIG. 5B shows a screen displayed on the monitor 4 in the state of FIG. 5A, and the target 58 such as the stomach wall is displayed on the monitor 4. The monitor 4 further displays a cross mark 62 indicating the center of the image and an irradiation position mark 64 of the light source beam 60 in a superimposed manner. In this way, it is possible to know the irradiation position of the light source beam 60 on the target 58 displayed on the monitor 4. With this display, it is possible to observe the target 58 and irradiate a desired position with the light source beam 60 so as to measure Raman scattering at the position.

FIG. 5C schematically shows a cross section in the state where the image capturing optical system is set close to the target 58 while maintaining the wide end of the zoom. In this way, by approaching the target, an image of a part of the target 58 is enlarged and formed on the CIGS image sensor 34. Note that the image-capturing lens 32 is adjusted in focus and extended by the automatic focus function. Also in this state, a positional relationship between the light source beam 60 emitted from the beam irradiation optical system 46 and the optical axis 48 of the image-capturing lens 32 is not changed. However, because an image capturing range is decreased, the light source beam 60 irradiates a position closer to the periphery of the image capturing range. FIG. 5D shows a screen displayed on the monitor 4 in the state of FIG. 5C, in which the target 58 is enlarged and displayed, and the irradiation position mark 64 of the light source beam 60 is displayed apart from the cross mark 62 to move closer to the periphery of the field of view of the monitor 4 compared with FIG. 5B.

FIG. 5E schematically shows a cross section in the state where the image-capturing lens 32 is zoomed in toward a telephoto side while maintaining the imaging distance in FIG. 5A. In this way, by zooming, an image of a part of the target 58 is enlarged and formed on the CIGS image sensor 34. In this case, the zoom driver 38 drives the image-capturing lens 32 so that a focal length of the image-capturing lens 32 is increased. Also in this state, a positional relationship between the light source beam 60 emitted from the beam irradiation optical system 46 and the optical axis 48 of the image-capturing lens 32 is not changed. However, because the image capturing range is decreased similarly to FIG. 5C, the light source beam 60 irradiates a position closer to the periphery of the image capturing range. FIG. 5F shows a screen displayed on the monitor 4 in the state of FIG. 5E. Similarly to FIG. 5D, the target 58 is enlarged and displayed, and the irradiation position mark 64 of the light source beam 60 is displayed apart from the cross mark 62 to move closer to the periphery of the field of view on the monitor 4 compared with FIG. 5B. As described above, a typical state is shown in FIG. 5, but it is possible to capture the image with a desired magnification by changing the imaging distance and zooming of the image-capturing lens 32. Further, moving of the irradiation position mark 64 in the field of view of the monitor 4 as shown in FIGS. 5B, 5D, and 5F can be performed by focal length information of the image-capturing lens 32 in zooming and focus adjustment state information of the image-capturing lens 32 in the focus driver 36.

Figure 6:
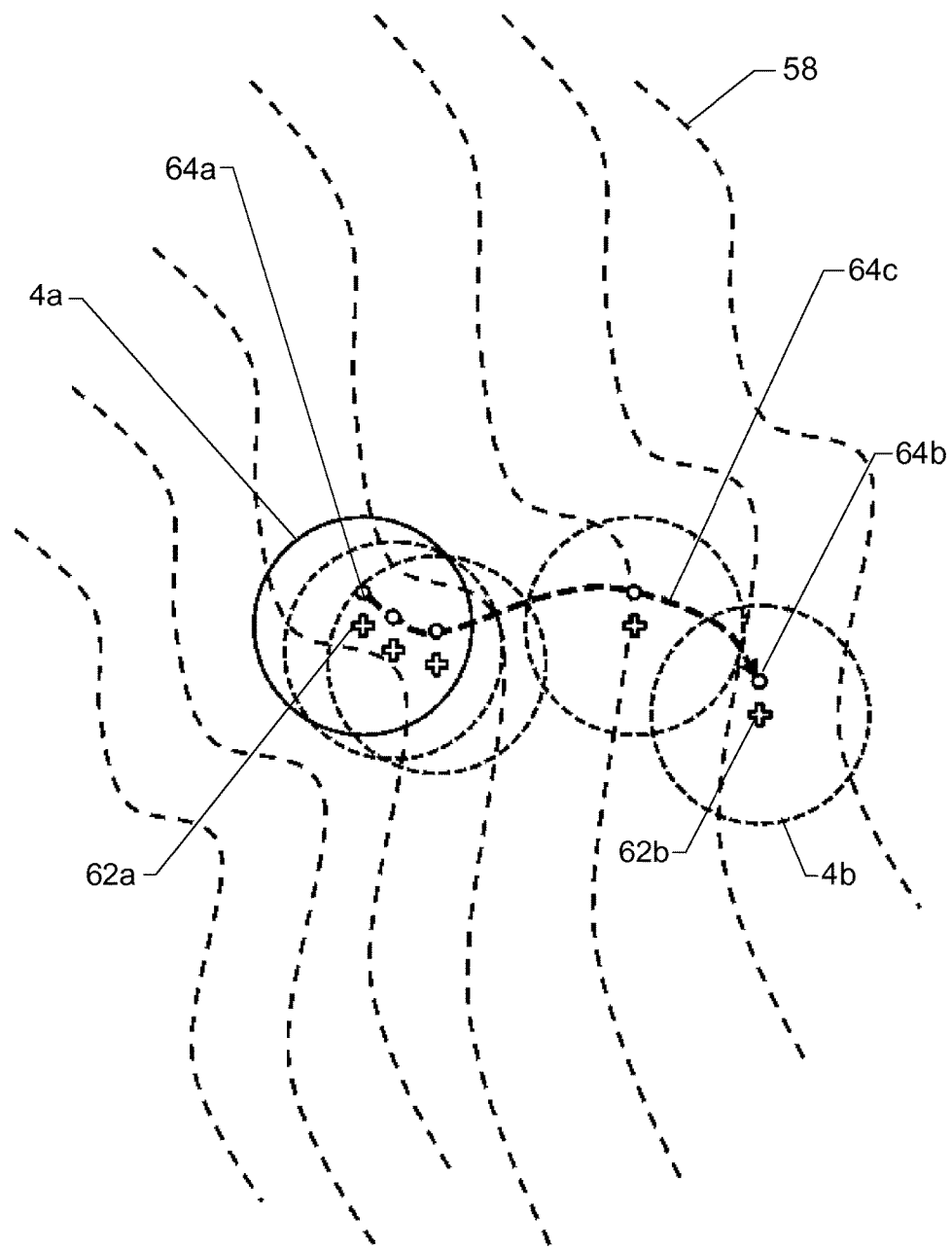
FIG. 6 is a schematic diagram showing a displaying range of the monitor shown in FIG. 5 with a relatively wide range of a target.

FIG. 6 is a schematic diagram showing a displaying range of the monitor 4 shown in FIG. 5B with a relatively wide range of the target 58 such as a stomach wall, and shows a manner in which the tip portion 12 is bent so that a relatively wide range of the target 58 is scanned and preliminarily measured. This preliminary measurement by scanning corresponds to setting the endoscope to a preliminary measurement mode in which the target 58 displayed on the monitor 4 is observed, and a part seemed to be normal as a visible image is moved from a display range 4a to a display range 4b in FIG. 6, for example. With this preliminary measurement by scanning, the light source beam 60 moves from an irradiation position mark 64a to an irradiation position mark 64b via a locus 64c. During this period, the Raman scattering processor 54 repeats actual measurement of Raman scattering intensity on the basis of the output of the CIGS image sensor 34, accumulates and stores the measured values, and stores an average value of the stored values as a measurement reference value. By determining the reference value based on the preliminary measurement in the early stage of measurement, it is possible to regard the reference value based on the actual measurement as Raman scattering intensity of a normal tissue and to compare Raman scattering intensity of a target section by actual measurement with the reference value. Thus, it is possible to determine whether or not the tissue of the target section in the actual measurement is normal.

Figure 7:
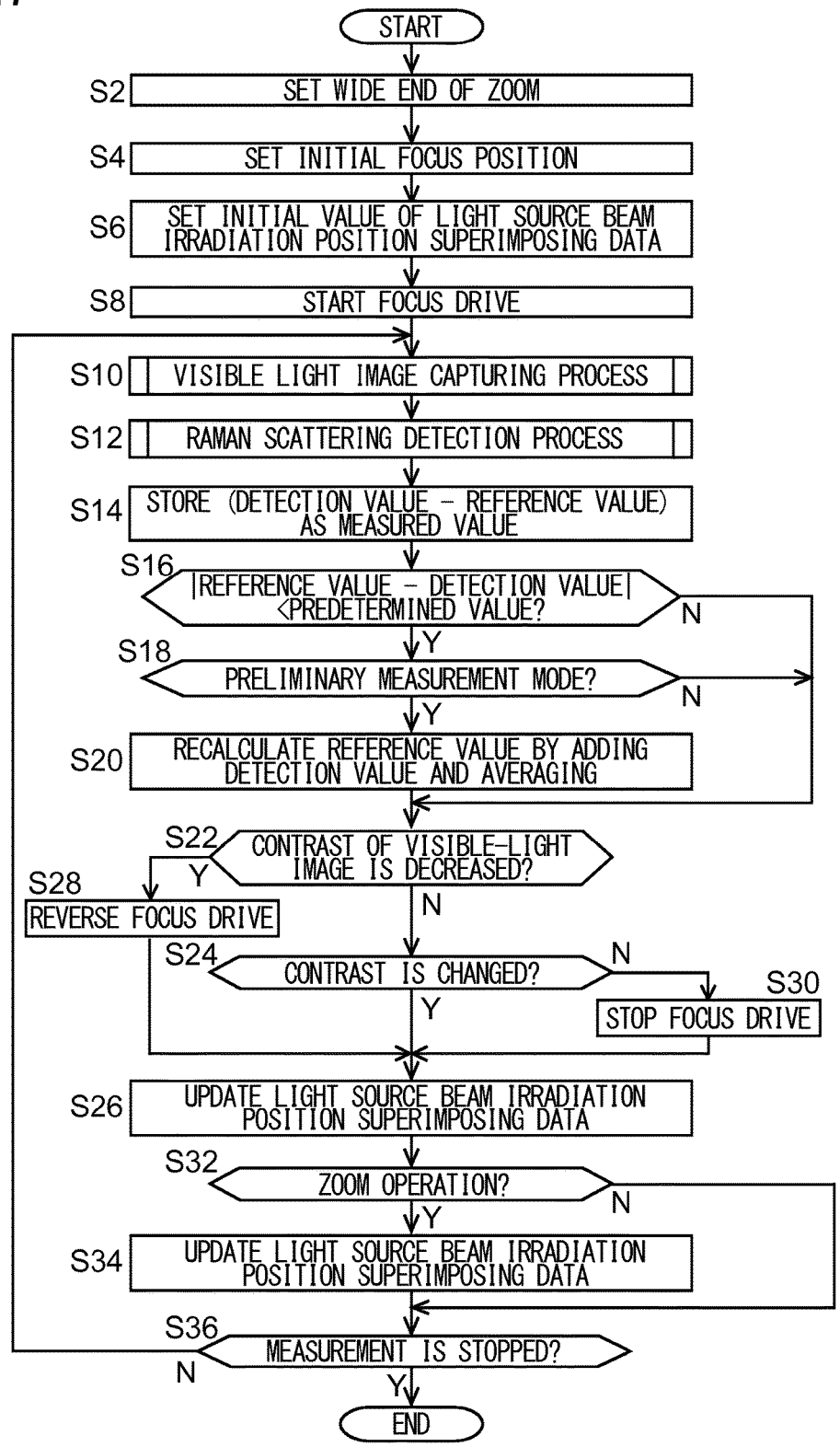
FIG. 7 is a basic flowchart of operation of a controller of Example 1 shown in FIG. 2.

FIG. 7 is a basic flowchart of operation of the controller 14 of the endoscope of Example 1 shown in FIG. 2. When a measurement start operation is made, the flow starts. In Step S2, the image-capturing lens 32 is initially set to the wide end of the zoom. In Step S4, an initial focus position (e.g., a position having a relatively long imaging distance and a large depth of focus) is set. Next in Step S6, an initial value of data for superimposed display of the light source beam irradiation position mark 64 on the monitor 4 is set on the basis of zoom setting and focus setting described above. After the initial settings described above, in Step S8, focus drive in an initial direction (e.g., in a direction of decreasing the imaging distance) is started. Because the automatic focus of Example 1 is a contrast type, it is necessary to first move the image-capturing lens 32 to check a variation of contrast, and then focus adjustment can be performed.

Further in Step S10, a visible light image capturing process is performed under illumination by the visible light LEDs (24, 26, and 28). Thus, a visible-light image in the field of view can be obtained, and contrast information for automatic focus can be obtained. Details of the visible light image capturing process in Step S10 will be described later. Further in Step S12, a Raman scattering detection process is performed under irradiation with the light source beam from the Raman scattering light source laser 30 so as to obtain a detection value. Details of the Raman scattering detection process in Step S12 will be also described later.

When the visible light image and the detection value of Raman scattering are obtained once respectively in Step S10 and Step S12, the process proceeds to Step S14 in which the reference value (or a predetermined initial value if there is no measured value) is subtracted from the detection value of Raman measurement, and the result is recorded as a measured value. Next in Step S16, it is checked whether or not an absolute value of difference between the reference value and the detection value is a predetermined value or smaller. If the absolute value of difference is the predetermined value or smaller, the process proceeds to Step S18 in which it is checked whether or not the current mode is the preliminary measurement mode. Then, if the current mode is the preliminary measurement mode, the process proceeds to Step S20 in which the reference value is recalculated by adding the detection value of this time and recalculating the average, and the process proceeds to Step S22. As described later, the process from Step S10 to Step S20 is repeated in the preliminary measurement shown in FIG. 6, and the reference value based on the average of the measured values is set in this repetition. If the absolute value of difference between the reference value and the measured value is larger than the predetermined value in Step S16, or if it is checked that the current mode is not the preliminary measurement mode in Step S18, the detection value of this time is not reflected on the reference value, and the process proceeds directly to Step S22.

In Step S22, it is checked whether or not the contrast of the captured visible-light image of this time is decreased from that of the last time. If the contrast is not decreased, the process proceeds to Step S24 in which it is checked whether or not the contrast is changed. If the contrast is changed, it means that the contrast is increased by the focus drive, and hence the focus drive in the direction is continued, and the process proceeds to Step S26. On the other hand, if a decrease of the contrast is detected in Step S22, it means that the image-capturing lens 32 is driven in the defocusing direction, and hence the process proceeds to Step S28 in which the focus drive is reversed, and the process proceeds to Step S26. In addition, if it is checked that the contrast is not changed in Step S24, it means that the contrast is at a peak so that the focus is adjusted, and hence the process proceeds to Step S30 in which the focus drive is stopped, and the process proceeds to Step S26. In Step S26, in either case, light source beam irradiation position superimposing data is updated on the basis of a new focus adjustment position, and the process proceeds to Step S32.

Further, as described later, the automatic focus control of Step S22, S24, S28 and S30 is repeatedly performed. During this repetition, if it is checked that the contrast is not decreased in Step S22 after the focus drive is stopped in Step S30, and if it is also checked that the contrast is not changed in Step S24, it means that the in-focus state is continued. In this case, stop of the focus drive is continued in Step S30, and the same data is maintained when updating data in Step S26 as a result. In addition, if it is checked that the contrast is decreased in Step S22 after the focus drive is stopped in Step S30, the focus drive is restarted in Step S28. The direction of the focus drive is opposite to that before the focus drive is stopped. If this is inappropriate, it is detected that the contrast is further decreased in Step S22 of the next repetition. Then, the process proceeds to Step S28 again, and the focus drive direction is corrected.

In Step S32, it is checked whether or not a zoom operation is made. If the zoom operation is made, the process proceeds to Step S34 in which the light source beam irradiation position superimposing data is updated on the basis of a new focal length as a result of the zoom operation, and the process proceeds to Step S36. On the other hand, if it is not checked in Step S32 that the zoom operation is made, the process proceeds directly to Step S36.

In Step S36, it is checked whether or not measurement stop operation is made. If it is not checked that the operation is made, the process returns to Step S10. Then, as long as the measurement stop operation is not checked in Step S36, the process of Step S10 to Step S36 is repeated, in which capturing of a visible-light image and measurement of Raman scattering are continued. On the other hand, if the measurement stop operation is checked in Step S36, the flow is finished at once.

Figure 8:
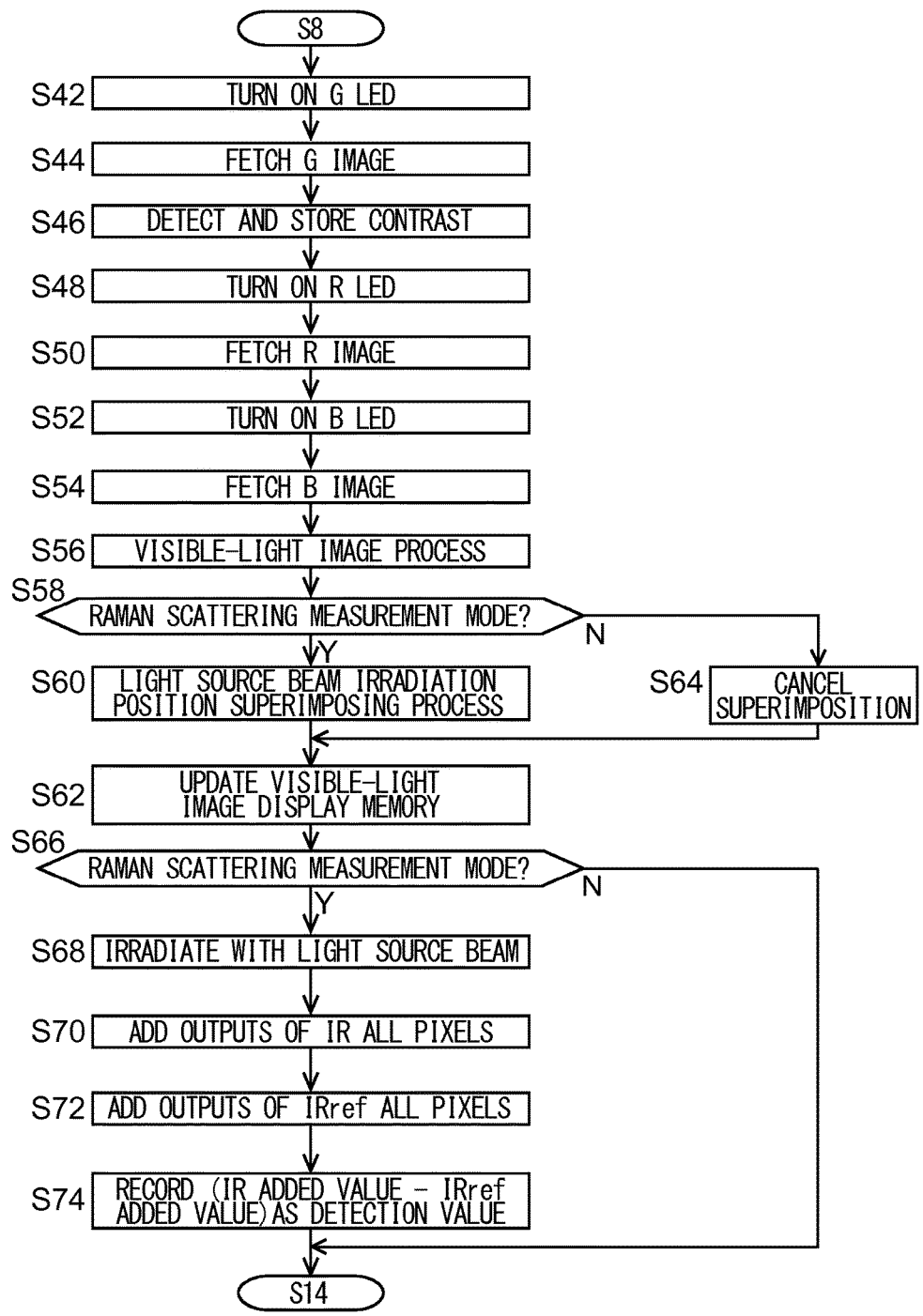
FIG. 8 is a flowchart showing details of Step S10 and Step S12 in FIG. 7.

FIG. 8 is a flowchart showing details of the visible light image capturing process of Step S10 and the Raman scattering detection process of Step S12 in FIG. 7. In FIG. 7, when the process proceeds from Step S8 to Step S10, the process is in Step S42 in FIG. 8 in which the green color LED 26 is turned on, and in Step S44, outputs of pixels of the CIGS image sensor 34 on which the visible light range filters (V11 and V12) are disposed are fetched by the image processor 18 as the green color image. Then, in Step S46, the contrast of the fetched green color image is detected and stored.

Next, in Step S48, the red color LED 24 is turned on, and in Step S50, the outputs of pixels of the CIGS image sensor 34 on which the visible light range filters (V11 and V12) are disposed are fetched by the image processor 18 as the red color image. In the same manner, in Step S52, the blue color LED 28 is turned on, and in Step S54, the outputs of pixels of the CIGS image sensor 34 on which the visible light range filters (V11 and V12) are disposed are fetched by the image processor 18 as the blue color image. Then, the process proceeds to Step S56.

In Step S56, as to each of the green color image, the red color image, and the blue color image fetched as described above, the interpolation is performed for the pixels on which measurement infrared filter (IR12) and the reference infrared filter (IRref21) are disposed, and the visible-light image is obtained and recorded on the basis of the green color image, the red color image, and the blue color image after the interpolation.

Next, in Step S58, it is checked whether or not the current mode is the Raman scattering measurement mode. If it is true, in Step S60, the irradiation position of the light source beam 60 is superimposed and displayed on the visible-light image, and the process proceeds to Step S62. On the other hand, if it is checked that the current mode is not the Raman scattering measurement mode in Step S58, the process proceeds to Step S64 in which the superimposition of the light source beam irradiation position is cancelled, and the process proceeds to Step S62. For instance, if there is no intention of measuring the Raman scattering when the endoscope is inserted or in other cases, the superimposed display of the light source beam irradiation position is bothering and causes misunderstanding. Accordingly, as described above, if the current mode is not the Raman scattering measurement mode, the superimposed display of the light source beam irradiation position is cancelled. Further, if the Raman scattering measurement mode is not selected from the beginning, nothing is performed in Step S64, and the process proceeds to Step S62.

In Step S62, the display data in the display memory 20 is updated by the display data on which the light source beam irradiation position is superimposed if necessary on the new visible-light image obtained in Step S56. Further, as long as there is no update of the display data as described above, the display memory 20 stores the last display data, and the display on the monitor 4 based on the last display data is continued also during the Raman scattering measurement. Then, if there is an update of the display data, the display on the monitor 4 is also updated.

Next, in Step S66, it is checked again whether or not the current mode is the Raman scattering measurement mode. If it is true, the light source beam 60 is emitted in Step S68, and the outputs of all pixels on which the measurement infrared filter (IR12) is disposed are added in Step S70. Then, in Step S72, the outputs of all pixels on which the reference infrared filter (IRref21) is disposed are added, and the process proceeds to Step S74. In Step S74, the added value of the outputs of all pixels on which the reference infrared filter (IRref21) is disposed is subtracted from the added value of the outputs of all pixels on which the measurement infrared filter (IR12) is disposed, and the result is recorded as the detection value. Then, the process proceeds to Step S14 in FIG. 7.

Various features of the present invention are not limited to the Examples described above and can be used in other various examples as long as the advantages can be enjoyed. For instance, measurement of the visible-light image in Example 1 is performed by the visible light range filter disposed on the CIGS image sensor and the time-shared light emission of the red color, green color, and blue color LEDs, but this is not a limitation. For instance, it is possible to dispose the red color filter, the green color filter, the blue color filter, the measurement infrared filter, and the reference infrared filter on the CIGS image sensor in an appropriate pattern, so as to obtain the visible-light image with illumination by a white color light source without time sharing.

In addition, the light source portion 22 is disposed in the controlling unit 2 in Example 1, but it may be disposed in the tip portion 12 so that the optical fiber thereto can be eliminated, and communication with the controlling unit 2 may be performed only with electric signals. Further, the automatic focus processor 52 and the Raman scattering processor 54 are disposed in the operation unit 6 in Example 1, but they may be disposed in the controlling unit 2. As to the focus adjustment, the automatic focus is adopted in Example 1, but a manual focus may be adopted. Also in this case, information of result of the manual focus adjustment is reflected on correction of the superimposed display of the light source beam irradiation position.

Example 2

Figure 9:
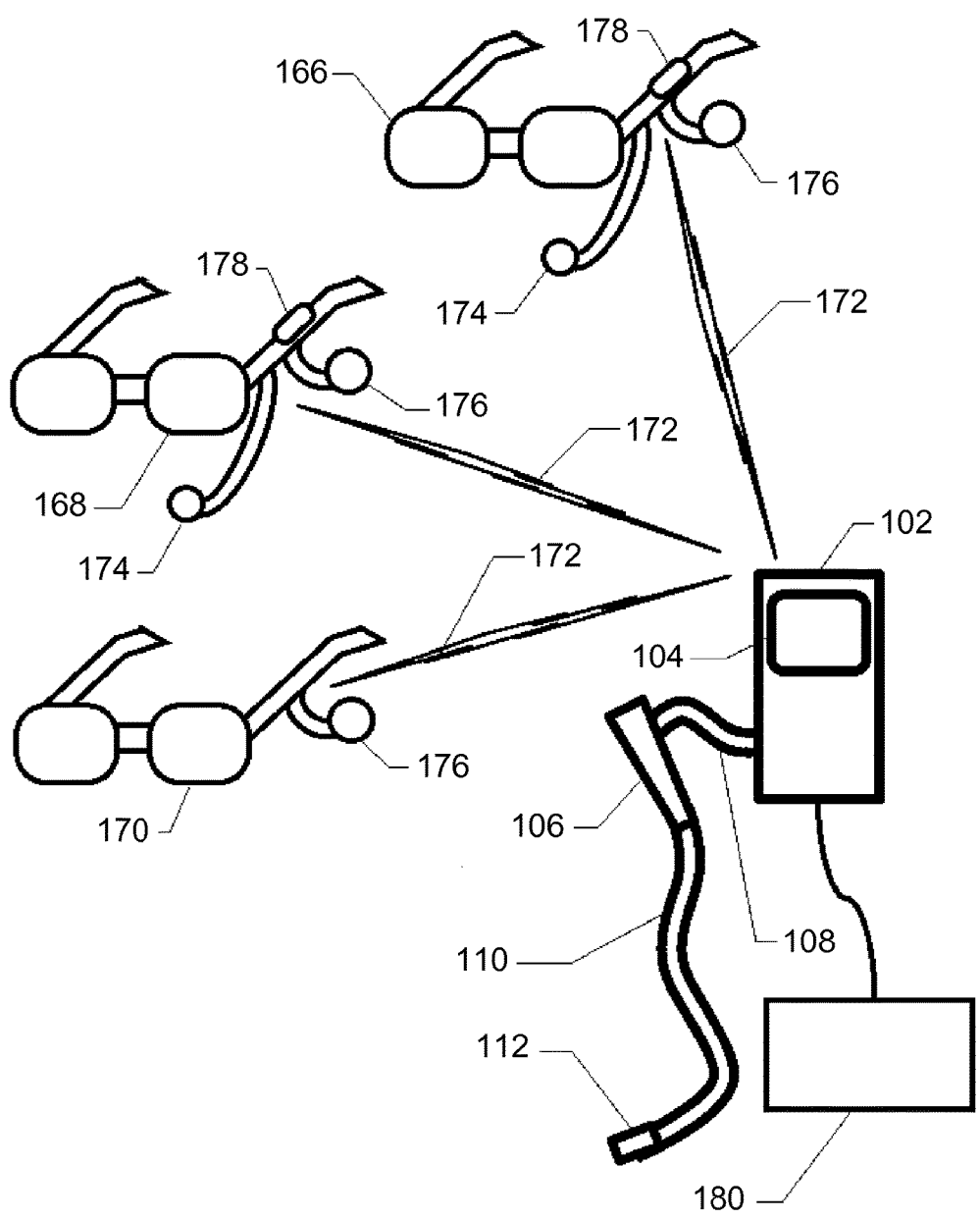
FIG. 9 is a schematic diagram showing a general structure of Example 2 of an endoscope system according to the present invention (Example 2).

FIG. 9 is a schematic diagram showing a general structure of Example 2 of the endoscope system according to the embodiment of the present invention. Element of the endoscope system of Example 2 are denoted by numerals of one hundreds, and among them, the same element of the endoscope part as that in Example 1 is denoted by numeral having the same digits of tens and ones places, and description thereof is omitted unless otherwise necessary.

The endoscope system of Example 2 shown in FIG. 9 includes the endoscope including a general unit 102, an operation unit 106, a connection cable 108, an insertion portion 110, and a tip portion 112. The structure of the endoscope has the same elements as the endoscope of Example 1 as described above, and different points from Example 1 will be described later.

The endoscope system of Example 2 shown in FIG. 9 further includes a spectacle-type wearable monitor for operator 166 to be worn by an operator who operates the endoscope, a spectacle-type wearable monitor for staff 168 to be worn by a medical staff member who cooperates with the operator, and a spectacle-type wearable monitor for patient 170 to be worn by a patient. Note that these names are based on supposition of medical scenes. In the case of examination, the spectacle-type wearable monitor for staff 168 is worn by a medical staff member of the examination team, and the spectacle-type wearable monitor for patient 170 is read as a "spectacle-type wearable monitor for examinee 170". In addition, only one spectacle-type wearable monitor for staff 168 is illustrated for simplification, but usually a plurality of spectacle-type wearable monitors for staff 168 are used for a plurality of staff members.

The spectacle-type wearable monitor for operator 166 is basically configured not to block the field of view so as not to interfere with a medical operation or a diagnostic operation, and the endoscope image and diagnosis information are superimposed and displayed on a part or a whole of the field of view. In addition, it is possible to display the endoscope image or the diagnosis information in the entire field of view by switching.

The spectacle-type wearable monitor for operator 166 can communicate with the general unit 102 via a short range wireless radio wave 172, receives endoscope image information and the diagnosis information from the general unit 102, and displays the endoscope image and the diagnosis information in the field of view. Further, as described later, the spectacle-type wearable monitor for operator 166 can provide a stereoscopic image (hereinafter referred to as a "3D image"), an image for right eye and an image for left eye are displayed in the fields of view of the right eye and the left eye, respectively.

The spectacle-type wearable monitor for operator 166 is further provided with a microphone 174 and an earphone 176, and conversation on medical side can be performed with the spectacle-type wearable monitor for staff 168 via the short range wireless communication with the general unit 102. Via the short range wireless communication with the general unit 102 or from the microphone 174, explaining announcement can be transmitted to the spectacle-type wearable monitor for patient 170. Further, in order not to discomfort the patient, when conversation is made on the medical side, a signal for muting the sound from the microphone 174 not to be transmitted to the spectacle-type wearable monitor for patient 170 can be transmitted to the general unit 102 by operation with an operation portion 178.

The general unit 102 of Example 2 is further connected to an external measurement device 180 arranged to measure blood pressure, pulse, $SaO_2$ (arterial oxygen saturation by a pulse oximeter or the like), body temperature, and the like. The measured information of the patient by the external measurement device 180 is also transmitted via the short range wireless radio wave 172 from the general unit 102 to the spectacle-type wearable monitor for operator 166 and is displayed in the field of view.

The structure of the spectacle-type wearable monitor for operator 166 described above enables the endoscope image and the diagnosis information to be displayed in the field of view for the operator without facing a monitor 104 of the general unit 102 in a posture continuing the medical operation or the diagnosis operation. Accordingly, it is possible to operate the endoscope not in an unnatural posture twisting the neck but in a posture facing the patient. In addition, because the information of the external measurement device 180 is also displayed in the field of view, it is possible to grasp the information in a posture for the medical operation or the diagnosis operation without twisting the neck for viewing the display on the external measurement device 180.

Because the structure of the spectacle-type wearable monitor for staff 168 is basically the same as that of the spectacle-type wearable monitor for operator 166, the corresponding portion is denoted by the same numeral, and description thereof is omitted unless otherwise necessary. In the same manner as the spectacle-type wearable monitor for operator 166, the spectacle-type wearable monitor for staff 168 receives the endoscope image information and the diagnosis information from the general unit 102 and displays the endoscope image and the diagnosis information in the field of view. In addition, the information of the external measurement device 180 is also displayed in the field of view.

In this way, the medical staff can share the information in real time with the operator in a posture for the medical operation or the diagnosis operation corresponding to each role. In other words, it is not necessary that all medical staff members should face the monitor 104. In addition, if a medical staff member wants to spontaneously ask a question to the operator, the staff member can transmit a signal of the question to the general unit 102 by operating the operation portion 178. Then, the microphone 174 of the spectacle-type wearable monitor for staff 168 is turned on. In order not to discomfort the patient when the patient hear conversation on the medical side including a question from a staff member and an answer of the operator, the earphone of the spectacle-type wearable monitor for patient 170 is muted after the operation portion 178 is operated. Further, the muting can be appropriately cancelled by operation by the operator.

Because the structure of the spectacle-type wearable monitor for patient 170 is basically the same as that of the spectacle-type wearable monitor for operator 166, the corresponding portion is denoted by the same numeral, and description thereof is omitted unless otherwise necessary. However, as to the spectacle-type wearable monitor for patient 170, only the endoscope image information is transmitted from the general unit 102, while the diagnosis information and the information of the external measurement device 180 that may discomfort the patient or may cause misunderstanding are not transmitted. Further, as described above, the explaining announcement of the operator is output to the earphone 176 of the spectacle-type wearable monitor for patient 170 via the general unit 102. In addition, in order to prevent confusion, the spectacle-type wearable monitor for patient 170 is dedicated to reception and is not equipped with a microphone.

With the structure described above, by wearing the spectacle-type wearable monitor for patient 170, the patient can observe the endoscope image information of themselves in a posture for the examination without twisting the neck toward the monitor 104, and hence can be examined without anxiety by receiving the appropriate explaining announcement from the operator.

Figure 10:
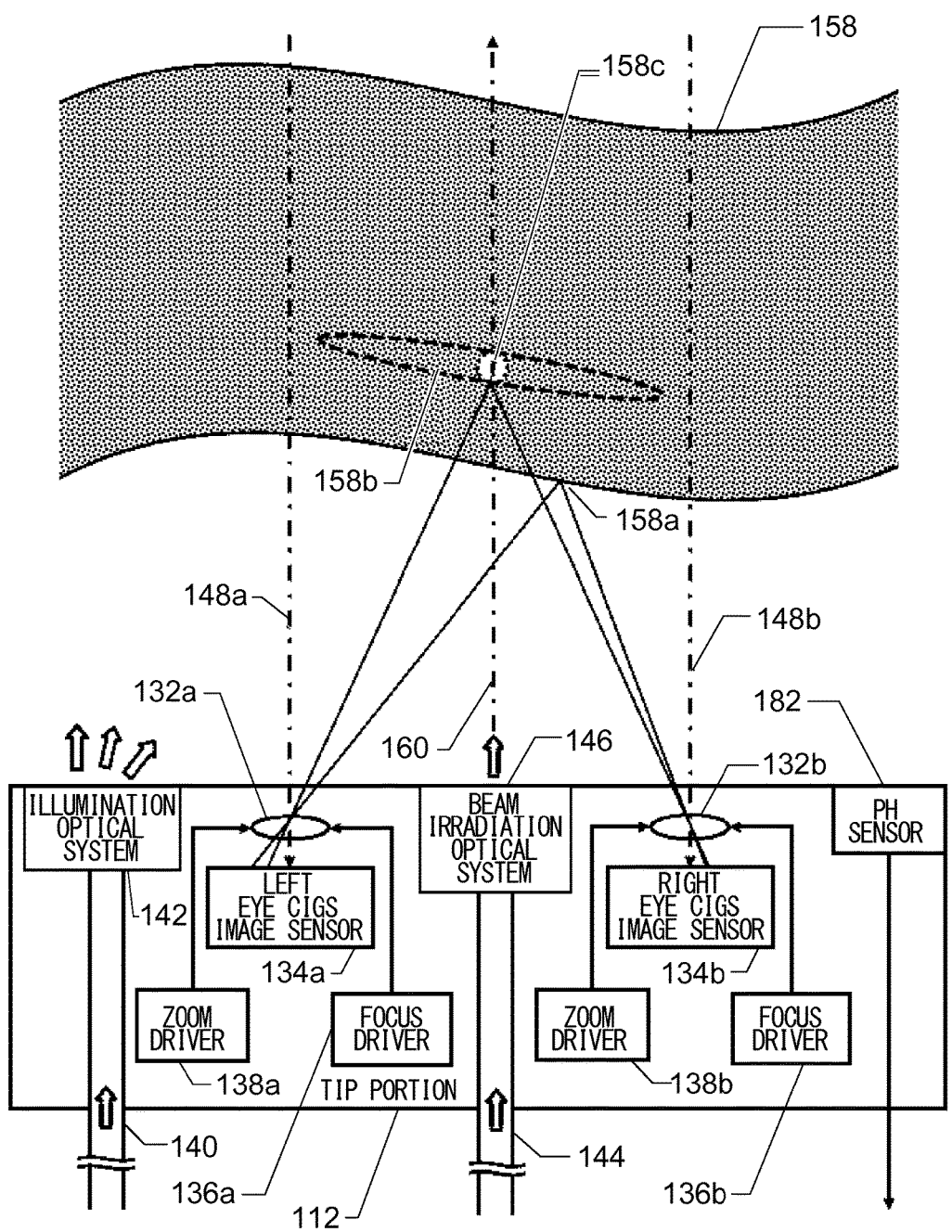
FIG. 10 is a block diagram of a tip portion of the endoscope of Example 2 shown in FIG. 9.

FIG. 10 is a block diagram of the tip portion 112 of the endoscope of Example 2 shown in FIG. 9, and a portion corresponding to that in FIG. 9 is denoted by the same numeral. The tip portion 112 of Example 2 is provided with an image-capturing lens 132a, a CIGS image sensor 134a, a focus driver 136a, and a zoom driver 138a in the same manner as in Example 1. Further in the Example, another set of an image-capturing lens 132b, a CIGS image sensor 134b, a focus driver 136b, and a zoom driver 138b is disposed in the same manner in order to obtain a 3D image. The former set is for left eye, and the latter set is for right eye. Optical axes 148a and 148b of them are parallel to each other.

In addition, in Example 2, a beam irradiation optical system 146 is disposed between the image-capturing lenses 132a and 132b, and a light source beam 160 from the Raman scattering light source laser 30 is guided in a laser optical fiber 144 to emerge in parallel to the optical axes 148a and 148b of the image-capturing lenses 132a and 132b. Further, also in Example 2, in the same manner as Example 1, the visible illumination light emitted sequentially from the red color LED 24, the green color LED 26, and the blue color LED 28 are guided in an illumination optical fiber 140 so as to illuminate the widest-angle ranges of view of the image-capturing lenses 132a and 132b from an illumination optical system 142. Note that the tip portion 112 of Example 2 is provided with a pH sensor 182 for measuring pH of gastric juice, for example. The internal measured value of the endoscope is also displayed in the fields of view of the spectacle-type wearable monitor for operator 166 and the spectacle-type wearable monitor for staff 168 via communication with the general unit 102.

In Example 2, with the binocular image capturing system described above, a 3D image of a surface 158a of a target tissue 158 is captured by the left eye CIGS image sensor 134a and the right eye CIGS image sensor 134b with visible light, and the captured right eye image and left eye image are respectively displayed in the fields of view of right eye and the left eye of the spectacle-type wearable monitors (166, 168, and 170).

Next, detection of the Raman-scattered light is described. As shown in FIG. 10, if an abnormal tissue 158b to be detected is relatively thin, a region 158c in which the abnormal tissue 158b responds to the light source beam 160 from the Raman scattering light source laser 30 may be expected to be a relatively narrow region. When the Raman-scattered light from this region 158c is received by the left eye CIGS image sensor 134a and the right eye CIGS image sensor 134b, each output image has an expansion due to scattering. If a barycenter of the intensity distribution is detected, a shift between barycenter positions detected by the left eye CIGS image sensor 134a and the right eye CIGS image sensor 134b is determined so that information in the direction of the light source beam 160 in the region 158c can be obtained.

Figure 11:
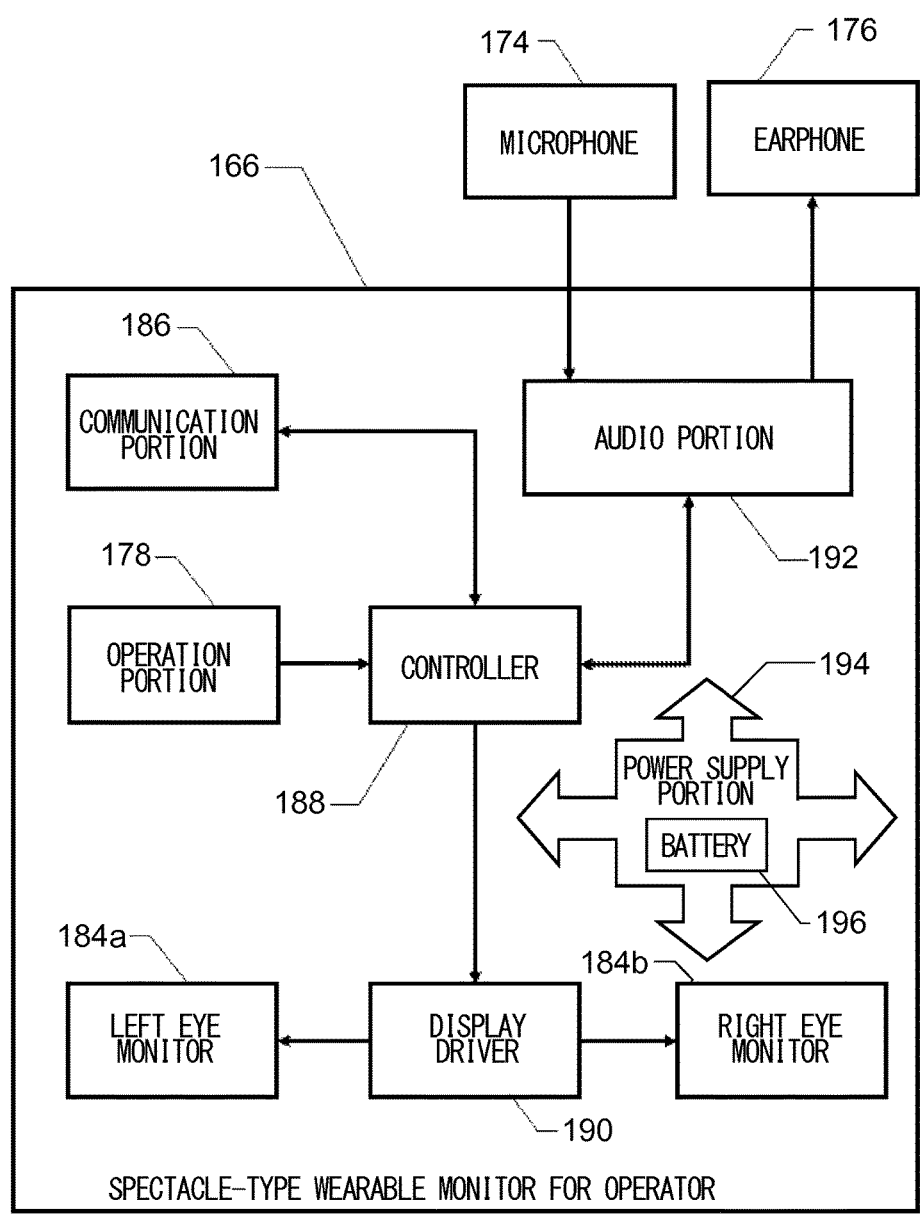
FIG. 11 is a block diagram of a spectacle-type wearable monitor for operator of Example 2 shown in FIG. 9.

FIG. 11 is a block diagram of the spectacle-type wearable monitor for operator 166 of Example 2 shown in FIG. 9, a portion corresponding to that in FIG. 9 is denoted by the same numeral. The spectacle-type wearable monitor for operator 166 of Example 2 shown in FIG. 11 includes a left eye monitor 184a and a right eye monitor 184b providing the left eye and the right eye with virtual images for display. The image signals for display are received by a communication portion 186 from the general unit 102 and are provided respectively to the left eye monitor 184*a* and the right eye monitor 184*b* via a controller 188 and a display driver 190.

On the other hand, an audio signal such as voice of staff is received by the communication portion 186 from the general unit 102 and is output to the earphone 176 via the controller 188 and an audio portion 192. In addition, the voice of the operator input from the microphone 174 is transmitted via the audio portion 192 and the controller 188 from the communication portion 186 to the general unit 102.

In addition, an operation with the operation portion 178 is transmitted via the controller 188 from the communication portion 186 to the general unit 102. For instance, when the operator wants to issue a technical instruction only to the staff on the medical side instead of the explaining announcement to the patient, the operator can transmit a signal of muting the operator's voice not to be transmitted to the spectacle-type wearable monitor for patient 170 to the general unit 102 by operating the operation portion 178. Note that a power supply portion 194 supplies electric power from a battery 196 to individual portions of the spectacle-type wearable monitor for operator 166.

Because the inside structure of the spectacle-type wearable monitor for staff 168 is the same as that of the spectacle-type wearable monitor for operator 166 shown in FIG. 11, illustration and description thereof are omitted. In addition, the function thereof can be understood by reading with replacing terms of FIG. 11 on the basis of the description of FIG. 9. In addition, the inside structure of the spectacle-type wearable monitor for patient 170 can be understood by eliminating the microphone 174 and the operation portion 178 from FIG. 11.

Figure 12:
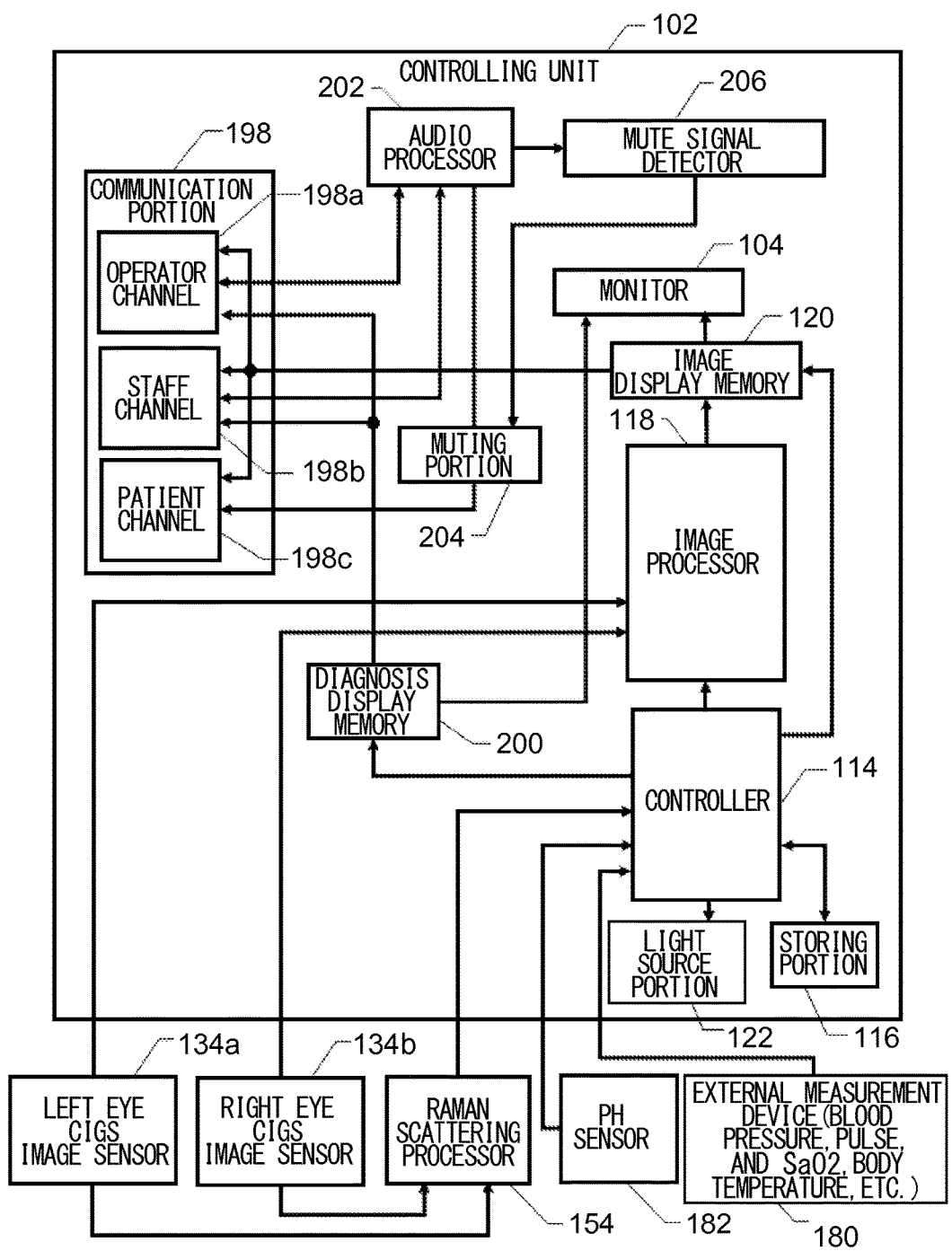
FIG. 12 is a block diagram of a general unit of Example 2 shown in FIG. 9.

FIG. 12 is a block diagram of the general unit 102 in Example 2 shown in FIG. 9, and a portion corresponding to that in FIG. 9 is denoted by the same numeral. In addition, the same portion as that in the block diagram of Example 1 shown in FIG. 2 is denoted by numeral of one hundreds having the same digits of tens and ones places as described above, and description thereof is omitted unless otherwise necessary.

A communication portion 198 of the general unit 102 shown in FIG. 12 includes an operator channel 198*a*, a staff channel 198*b*, and a patient channel 198*c*, for communicating with the spectacle-type wearable monitor for operator 166, the spectacle-type wearable monitor for staff 168, and the spectacle-type wearable monitor for patient 170, respectively.

Visible-light image information from an image display memory 120 and the diagnosis display information from a diagnosis display memory 200 are input to the operator channel 198*a* and the staff channel 198*b*. The diagnosis display information from the diagnosis display memory 200 is processed by a controller 114 on the basis of an input from a Raman scattering processor 154, an internal measurement input of the pH sensor 182 and the like, and an input from the external measurement device 180, and a result of the process is stored in the diagnosis display memory 200. Note that the diagnosis display information in the diagnosis display memory 200 is also transmitted to and displayed on the monitor 104.

In addition, the operator channel 198*a* and the staff channel 198*b* perform bi-directional information exchange with an audio processor 202. In this way, voice communication can be performed between the operator channel 198*a* and the staff channel 198*b*, and a mute signal based on an operation with the operation portion 178 received via the operator channel 198*a* or the staff channel 198*b* is transmitted to the audio processor 202.

On the other hand, the visible-light image information from the image display memory 120 is input to the patient channel 198*c*, but the diagnosis display information from the diagnosis display memory 200 is not input to the same. In addition, a one-directional sound signal from the audio processor 202 is input. In addition, this sound signal is input via a muting portion 204. When a mute signal detector 206 detects that a mute signal is transmitted to the audio processor 202, the muting portion 204 is controlled to mute the sound signal transmitted from the audio processor 202 to the patient channel 198*c*.

Figure 13:
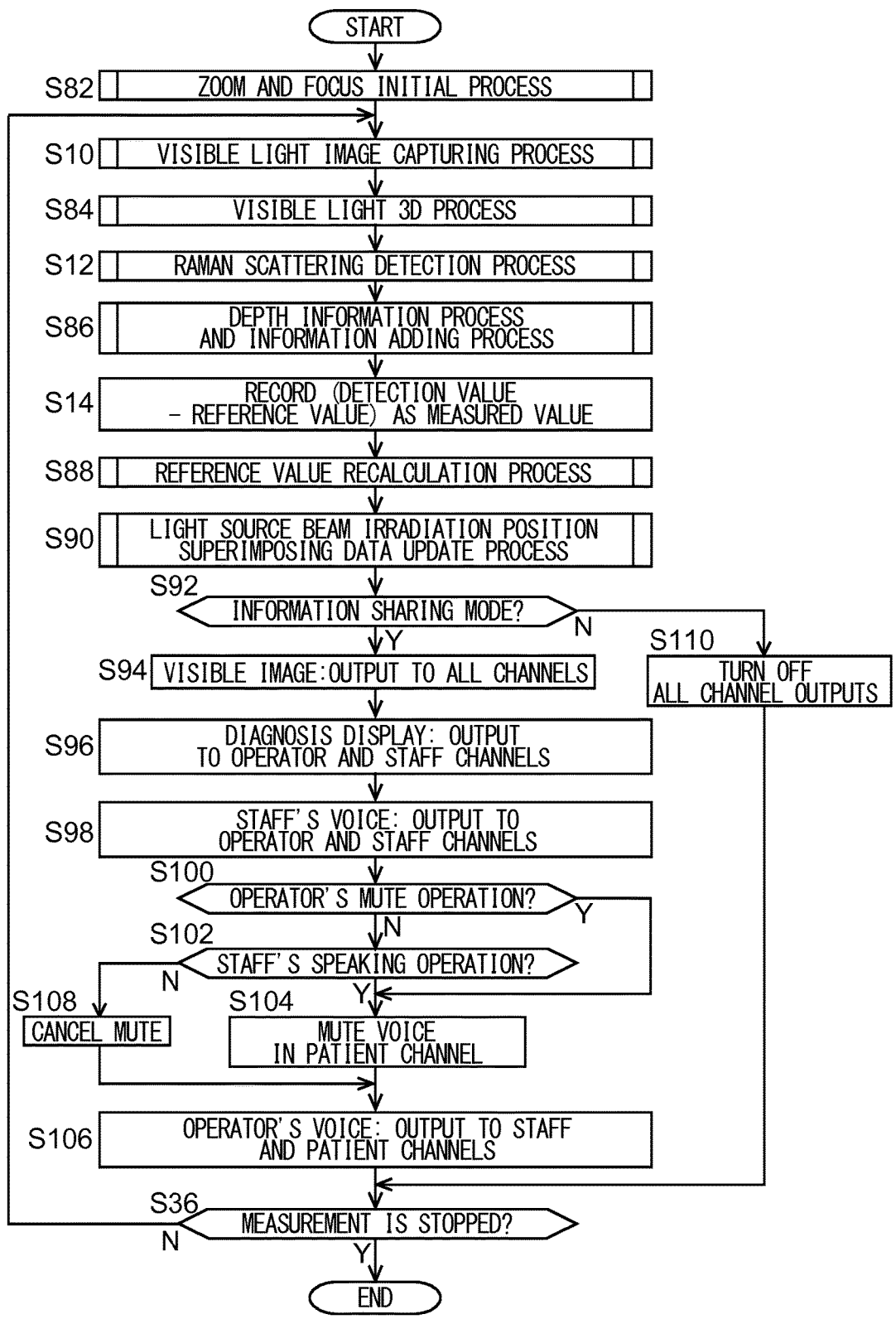
FIG. 13 is a basic flowchart of operation of the controller of Example 2 shown in FIG. 12.

FIG. 13 is a basic flowchart of an operation of the controller 114 of the general unit 102 in Example 2 shown in FIG. 12. When the measurement start operation is made, the flow starts. The flow shown in FIG. 12 is illustrated by referring to the flow of Example 1 shown in FIGS. 7 and 8. In addition, the same function is denoted by the same step number. Description thereof is omitted unless otherwise necessary. Step S82 in FIG. 13 is a summary of Steps S2 to S8 in FIG. 7. When the process proceeds from Step S82 via Step S10 to Step S84, a visible light 3D processing is performed, and the process proceeds to Step S12. Details of the visible light 3D processing in Step S84 will be described later.

In addition, when the Raman scattering detection process in Step S12 is finished, a depth information process and an information adding process in Step S86 are performed, and the process proceeds to Step S14. Details of Step S86 will be described later. Step S88 in FIG. 13 is a summary of the reference value recalculation function from Step S16 to Step S20 in FIG. 7. In addition, Step S90 in FIG. 13 is a summary of the light source beam irradiation position superimposing data update function due to the automatic focus or the manual zoom operation from Step S22 to Step S34 in FIG. 7.

The process from Step S92 to Step S106 corresponds to the function of the real-time information sharing by the spectacle-type wearable monitors (166, 168, and 170) described above with reference to FIGS. 9 and 12. When the flow proceeds from Step S90 to Step S92, it is checked whether or not the information sharing mode is set. If the information sharing mode is set, the process proceeds to Step S94 in which the visible image is output to all channels of the communication portion 198. Further in Step S96, the diagnosis display is output to the operator channel 198*a* and the staff channel 198*b*. Further in Step S98, voice of a staff member is output to the operator channel 198*a* and the staff channel 198*b*, and the process proceeds to Step S100.

In Step S100, it is checked whether or not the mute signal received via the operator channel 198*a* is detected by the mute signal detector 206. If it is not detected, the process proceeds to Step S102 in which it is checked whether or not the mute signal received via the staff channel 198*b* is detected by the mute signal detector 206. If it is detected, the process proceeds to Step S104 in which the voice in the patient channel 198*c* is muted, and the process proceeds to Step S106. Also in the case where the mute signal received via the operator channel 198*a* is detected in Step S100, the process proceeds to Step S104 in which the voice in the patient channel 198*c* is muted, and the process proceeds to Step S106. On the other hand, if the mute signal is not received via the operator channel 198*a* or the staff channel 198*b*, the process proceeds via Steps S100 to S102 to Step S108 in which the mute is cancelled, and the process proceeds to Step S106.

In Step S106, the voice of the operator is output to the operator channel 198*a* and the patient channel 198*c*, and the process proceeds to Step S36. In this case, if the voice in the patient channel 198c is muted in Step S104, the voice is not output to the spectacle-type wearable monitor for patient 170. Further, if the setting of the information sharing mode is not detected in Step S92, the process proceeds to Step S110 in which outputs to all channels (198a, 198b, and 198c) are turned off, and the process proceeds to Step S36. In Step S36, it is checked whether or not the measurement is stopped. If the measurement is not stopped, the process returns to Step S10. After that, the process of Steps S10, S84, S12, S86, S14, S88 to S110, and S36 is repeated as long as the stop of measurement is not detected in Step S36. On the other hand, if the stop of measurement is detected in Step S36, the flow is promptly finished.

Figure 14:
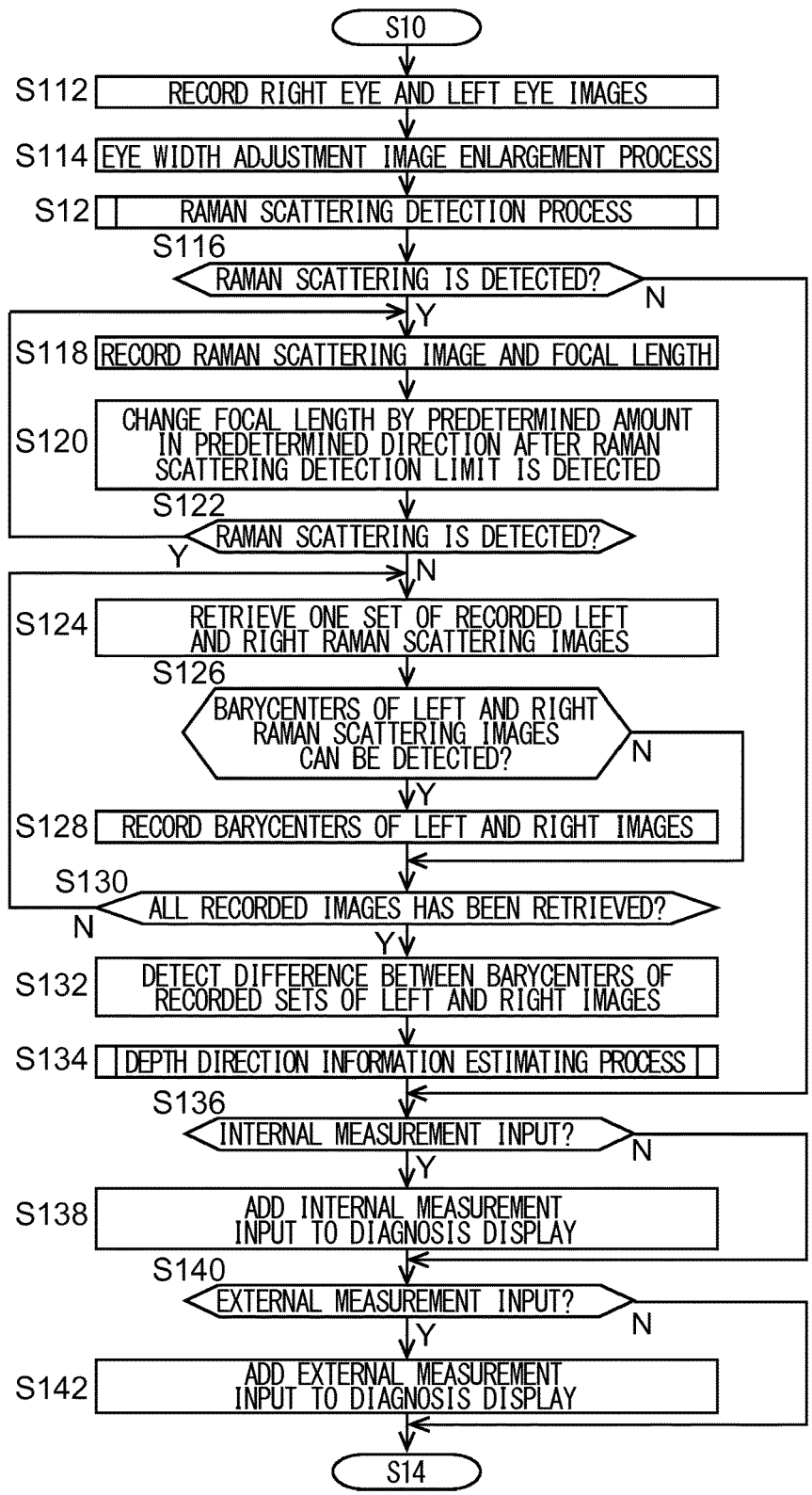
FIG. 14 is a flowchart showing details of Step S86 to which the process proceeds via Step S84 and Step S12 in FIG. 13.

FIG. 14 is a flowchart showing details of the visible light 3D processing in Step S84 of FIG. 13 and the depth information process and the information adding process in the Step S86 after Step S12. When the process proceeds to Step S112 via the visible light image capturing process under illumination by the visible light LEDs (24, 26, and 28) in Step S10, the visible-light images in the fields of view obtained on the basis of the image signals of the left eye CIGS image sensor 134a and the right eye CIGS image sensor 134b are recorded as the right eye image and the left eye image, respectively.

Next, in Step S114, an image enlargement process for eye width adjustment is performed. Because a distance between the optical axes 148a and 148b in the tip portion 112 is smaller than natural eye width, the images are enlarged so that a natural 3D image can be recognized when the images are displayed on the left eye monitor 184a and the right eye monitor 184b of the spectacle-type wearable monitor for operator 166 or the like. Step S112 and S114 described above are details of the visible light 3D processing in FIG. 13.

Next, the process proceeds to Step S116 via Step S12. Step S116 to Step S134 are details of the depth information process in Step S86 of FIG. 13, and Step S136 to Step S142 are details of the information adding process of Step S86 of FIG. 13.

First, it is checked whether or not the Raman scattering is detected in Step S116. If the Raman scattering is detected, the process proceeds to Step S118 in which the Raman scattering images of the left eye CIGS image sensor 134a and the right eye CIGS image sensor 134b at the detection time point are recorded. Further, information of a focal length at that time is also recorded in association with the Raman scattering image.

After the recording described above, the process proceeds to Step S120. Then, after detecting a limit of detection of the Raman scattering when the focus adjustment is performed, the focal length is changed by a predetermined amount in a predetermined direction from the limit, and the process proceeds to Step S122. In Step S122, after the focal length is changed, it is checked whether or not the Raman scattering is detected. If it is detected, the process proceeds to Step S118 in which the left and right Raman scattering images and information of the focal length are associated to each other and are recorded. After that, the process from Step S118 to Step S122 is repeated until the Raman scattering cannot be detected in Step S122, and a set of the left and right Raman scattering images at different focal lengths (sets of them if the abnormal tissue 158b shown in FIG. 10 has a thickness) are recorded.

If the Raman scattering cannot be detected in Step S122, the process proceeds to Step S124 in which a set of the recorded left and right Raman scattering images is retrieved, and the process proceeds to Step S126 in which it is checked whether or not barycenters of intensity distributions in the left and right Raman scattering images can be detected. If they can be detected, the barycenters of the left and right images detected in Step S128 are recorded, and the process proceeds to Step S130. In Step S130, it is checked whether or not all the recorded left and right Raman scattering images are retrieved. If there is a recorded image that is not retrieved, the process returns to Step S124, and the process from Step S124 to Step S130 is repeated until all the left and right Raman scattering images are retrieved. In this repetition, the barycenter positions of the left and right images for which the barycenter can be detected are recorded (there is a case where the barycenter position is not detected so that no record can be obtained).

If it is detected in Step S130 that all the recorded images are retrieved, the process proceeds to Step S132 in which a difference between the left and right barycenter positions is detected for each of the sets if there are sets of images having recorded barycenter positions. Then, a process of estimating information in the depth direction (in the direction of the light source beam 160) is performed in Step S134 on the basis of the difference between the detected barycenter positions, and the process proceeds to Step S136. Further, if the Raman scattering is not detected in Step S116, the process proceeds directly to Step S136.

In Step S136, a presence or absence of an input of the internal measured value of the pH sensor 182 or the like is detected. If there is the input, the process proceeds to Step S138 in which the input internal measured value is added to the diagnosis information, and the process proceeds to Step S140. On the other hand, if there is no internal measured value, the process proceeds directly to Step S140. In Step S140, a presence or absence of an input of an external measured value of the external measurement device 180 or the like is detected. If there is the input, the process proceeds to Step S142 in which the input external measured value is added to the diagnosis information, and the process proceeds to Step S14. On the other hand, if there is no input of the external measured value, the process proceeds directly to Step S14. A display image of the measurement input added in Step S138 or S142 is input to the diagnosis display memory 200 shown in FIG. 12, and is transmitted from the communication portion 198 so as to be displayed together with the endoscope image on the spectacle-type wearable monitor for operator 166 and the like.

The various features of the present invention are not limited to the Examples described above and can be applied to various other examples as long as the advantages thereof can be enjoyed. For instance, although Example 2 is configured as the cancer diagnostic device utilizing the Raman scattering, but the real-time information exchange among the operator, the staff, and the patient, the 3D processing, and the like using the spectacle-type wearable monitor can be applied to a normal endoscope and other diagnosis medical devices.

SUMMARY OF DISCLOSURE

Hereinafter, various invention aspects disclosed in this specification are summarized and described.

The invention disclosed in this specification provides a cancer diagnostic device including the CIGS image sensor provided with the visible-light-range filter and the Raman scattering detection filter. In this way, using the wide sensitivity range of the CIGS image sensor, it is possible to capture a visible light image of the target and to detect the Raman scattering.

According to the specific feature of the invention disclosed in this specification, the Raman scattering detection filter includes the measurement infrared filter that selectively transmits the Raman-scattered light and the reference infrared filter that selectively transmits the near-band infrared light without the Raman-scattered light. In this way, it is possible to cut the Rayleigh scattering and appropriately detect the Raman scattering.

According to another specific feature, the cancer diagnostic device includes the visible-light-range illumination light source and the Raman scattering light source, and the CIGS image sensor performs capturing of a visible-light image and detection of Raman scattering on the basis of the visible-light-range illumination light source and the Raman scattering light source. According to a more specific feature, the visible-light-range illumination light source and the Raman scattering light source irradiate the target in a time-shared manner. According to another specific feature, the visible-light-range illumination light source includes a plurality of colors of light sources that emit light in a time-shared manner, and the visible-light-range filter transmits light from each of the plurality of colors of light sources. According to another specific feature, the visible-light-range filter selectively transmits a plurality of colors of light.

According to another specific feature, the cancer diagnostic device is provided with the storing portion that stores the output of the CIGS image sensor with the Raman scattering detection filter as the reference value. In this way, it is possible to determine the reference value by preliminary measurement, for example, and to perform the actual measurement on the basis of the reference value. According to a more specific feature, the storing portion stores the average value of the plurality of measured values by the CIGS image sensor with the Raman scattering detection filter as the reference value.

According to another specific feature, in displaying of the visible-light image by the CIGS image sensor, the superimposed display is performed in which the sections where Raman scattering is detected are specified. In this way, it is possible to appropriately know the measured section of the Raman scattering on the basis of the visible-light image.

According to another feature of the invention disclosed in this specification, a cancer diagnostic device is provided, which includes an image-capturing lens so that the capturing of a visible-light image and the measurement of the Raman scattering can be performed, in which the superimposed display to specify the sections where Raman scattering is detected is performed in displaying of the visible-light image, and the superimposed display position can be changed in accordance with the focus adjustment of the image-capturing lens. In this way, it is possible to appropriately know the Raman scattering measured section on the basis of the visible-light image, and to correctly display the Raman scattering measured section in a superimposed manner regardless of the focus adjustment even if the section where Raman scattering is detected is not on the optical axis of the image-capturing lens.

According to another feature of the invention disclosed in this specification, the cancer diagnostic device is provided, which includes the image-capturing lens so that the capturing of a visible-light image and the measurement of the Raman scattering can be performed, in which the superimposed display to specify the sections where Raman scattering is detected is performed in displaying of the visible-light image, and the superimposed display position is changed in accordance with zooming of the image-capturing lens. In this way, it is possible to appropriately know the Raman scattering measured section on the basis of the visible-light image, and to correctly display the Raman scattering measured section in a superimposed manner regardless of the zooming even if the section where Raman scattering is detected is not on the optical axis of the image-capturing lens.

According to another feature of the invention disclosed in this specification, the cancer diagnostic device is provided, in which the capturing of a visible-light image and the measurement of the Raman scattering are performed in a time-shared manner, and the displaying of the visible-light image is continued even in the detection of Raman scattering. In this way, the capturing of a visible-light image and the measurement of the Raman scattering can be performed without interference to each other, and the displaying of the visible-light image can be performed without interrupted by the measurement of the Raman scattering.

In addition, the invention disclosed in this specification provides a diagnostic system including a diagnosis information acquiring portion arranged to obtain diagnosis information, and a plurality of wearable display devices arranged to perform short range wireless communication with the diagnosis information acquiring portion so as to display received diagnosis information. In this way, it is possible to share the diagnosis information in real time while maintaining a posture in the diagnosis operation or the like.

According to a specific feature, the diagnosis information acquiring portion provides at least one of the plurality of wearable display devices with the diagnosis information partially restricted from full information provided to other wearable display devices. Further, according to another feature, the diagnosis information acquiring portion determines whether or not to restrict the diagnosis information provided to the at least one of the plurality of wearable display devices. In this way, for example, provision of technical information is restricted when sharing information with the patient, and hence it can be prevented to cause anxiety to the patient. According to a more specific feature, the diagnosis information acquiring portion determines whether or not to restrict the diagnosis information provided to the at least one of the plurality of wearable display devices on the basis of an instruction from another wearable display device. Thus, for example, it is possible to restrict the information by an instruction from a person who has obtained the diagnosis information or a staff member who want to ask a technical question.

According to another more specific feature, at least one of the plurality of wearable display devices is worn by the examinee. Further, according to another more specific feature, the plurality of wearable display devices are worn by a plurality of examining staff members to share the diagnosis information. According to another more specific feature, the plurality of wearable display devices have telephoning means to talk among the plurality of examining staff members. According to a more specific feature, at least one of the plurality of wearable display devices is worn by the examinee, and there is provided mute means arranged to prevent the voice of the telephoning means from being transmitted to the wearable display device worn by the examinee.

According to another specific feature, the diagnosis information acquiring portion obtains 3D image information, and the plurality of wearable display devices include the 3D image display portion. In this way, it is possible to perform the diagnosis based on the 3D image information using the wearable display device.

According to another specific feature, another diagnosis information acquiring portion is provided, and the plurality of wearable display devices display also the diagnosis information obtained by the another diagnosis information acquiring portion. In this way, information pieces of the plurality of diagnosis information acquiring portions can be shared by the wearable display devices in a unified manner.

According to another feature of the invention disclosed in this specification, the diagnostic device is provided, which includes the diagnosis information acquiring portion having a distance between a pair of optical axes different from the eye width arranged to obtain 3D image information, and adjusting means arranged to adjust a difference between the distance between the pair of optical axes in the 3D image information and the eye width and to provide the adjusted result to the 3D image display portion. Thus, effective 3D image observation can be performed.

According to another feature of the invention disclosed in this specification, the diagnostic device is provided, which includes a diagnosis information acquiring portion arranged to obtain a pair of images as the 3D image information, means arranged to determine the barycenters of the pair of images, and analysis means arranged to analyze a difference between the barycenters of the pair of images. In this way, even if the obtained image is expanded due to scattering or the like, the information in the depth direction can be obtained by the 3D image.

According to another feature of the invention disclosed in this specification, the wearable display device is provided, which includes the short range wireless communication portion for exchanging information with another wearable display device, and the operation portion for restricting information to be provided to the another wearable display device. In this way, for example, it is possible to restrict provision of technical information when sharing information with the patient, and hence it can be prevented to cause anxiety to the patient. According to a more specific feature, the operation portion is used for restricting the information to be provided to one of the other wearable display devices from the information to be provided to the other wearable display devices.

INDUSTRIAL APPLICABILITY

The present invention can be applied to a diagnostic system, a diagnostic device, a displaying device for diagnosis, and a cancer diagnostic device.

EXPLANATION OF NUMERALS

V11, V22 visible-light-range filter
IR12, IRref21 Raman scattering detection filter
34 CIGS image sensor
IR12 measurement infrared filter
IRref21 reference infrared filter
24, 26, 28 visible-light-range illumination light source
30 Raman scattering light source
16 storing portion
4 display portion
64 superimposed display to specify sections where Raman scattering is detected
32 image-capturing lens
102 to 112 diagnosis information acquiring portion
166, 168, 170 wearable display device
174, 176 telephoning means
204 mute means
148a, 148 a pair of optical axes for obtaining 3D image information
114, 118 adjusting means
114, 118 means for determining barycenter
114, 118 analysis means
180, 182 another diagnosis information acquiring portion
134a, 134b CIGS image sensor
178 operation portion

The invention claimed is:

1. A cancer diagnostic device comprising:
a single CIGS image sensor having a plurality of pixels to capture an image; and
an image-capturing lens arranged to form an image of a measurement target on the pixels of the single CIGS image sensor,
wherein the single CIGS image sensor is provided with a visible-light-range optical filter disposed on at least one of the pixels and a Raman scattering detection optical filter disposed on at least another of the pixels,
wherein the Raman scattering detection filter includes a measurement infrared filter arranged to selectively transmit Raman-scattered light, and a reference infrared filter arranged to selectively transmit near-band infrared light excluding the Raman-scattered light, wherein outputs of all pixels on which the measurement infrared filters are disposed are added to obtain a first value, outputs of all pixels on which the reference infrared filters are disposed are added to obtain a second value, and a difference between the first and second values is calculated to detect intensity of the Raman-scattered light.

2. The cancer diagnostic device according to claim 1, further comprising a visible-light-range illumination light source and a Raman scattering light source, wherein the CIGS image sensor performs capturing of a visible-light image and detection of the Raman scattering on the basis of the visible-light-range illumination light source and the Raman scattering light source, respectively.

3. The cancer diagnostic device according to claim 1, further comprising a storing portion arranged to store an output of the CIGS image sensor with the Raman scattering detection filter as a reference value.

4. The cancer diagnostic device according to claim 3, wherein the storing portion stores an average value of a plurality of measured values by the CIGS image sensor with the Raman scattering detection filter as the reference value.

5. The cancer diagnostic device according to claim 1, wherein the capturing of a visible-light image by the CIGS image sensor and the detection of the Raman scattering are performed in a time-shared manner, wherein the cancer diagnostic device includes a display portion arranged to display the visible-light image, and wherein the displaying of the visible-light image by the display portion is continued also during the detection of the Raman scattering.

6. The cancer diagnostic device according to claim 1, wherein a superimposed display to specify sections where Raman scattering is detected is performed on the display of the visible-light image by the CIGS image sensor.

7. The cancer diagnostic device according to claim 6, wherein the superimposed display to specify sections where Raman scattering is detected is changed in accordance with focus adjustment of the image-capturing lens.

8. The cancer diagnostic device according to claim 6, wherein a position of the superimposed display to specify sections where Raman scattering is detected is changed in accordance with zooming of the image-capturing lens.

9. A diagnostic system comprising:
the cancer diagnostic device according to claim 1; and
a plurality of wearable display devices arranged to perform short range wireless communication with the cancer diagnostic device so as to display received diagnosis information.

10. A diagnostic system comprising:
a diagnosis information acquiring portion arranged to acquire diagnosis information wherein the diagnosis information acquiring portion included a cancer diagnostic device according to claim 1 to acquire the diagnosis information; and
a plurality of wearable display devices arranged to perform short range wireless communication with the diagnosis information acquiring portion so as to display received diagnosis information.

11. The diagnostic system according to claim 10, wherein the diagnosis information acquiring portion provides at least one of the plurality of wearable display devices with diagnosis information partially restricted from full information provided to other wearable display device.

12. The diagnostic system according to claim 10, wherein the plurality of wearable display devices have telephoning means to talk among a plurality of examining staff members.

13. The diagnostic system according to claim 12, wherein at least one of the plurality of wearable display devices is worn by an examinee, and wherein the diagnostic system includes mute means arranged to prevent the voice of the telephoning means from being transmitted to the wearable display device worn by the examinee.

14. The diagnostic system according to claim 10, wherein the diagnosis information acquiring portion acquires 3D image information, and wherein the plurality of wearable display devices include a 3D image display portion.

15. The diagnostic system according to claim 14, wherein a distance between a pair of optical axes for the diagnosis information acquiring portion to acquire the 3D image information is different from an eye width of the plurality of wearable display devices, and wherein the diagnostic system includes means arranged to adjust between the distance and the eye width.

16. The diagnostic system according to claim 10, wherein the diagnosis information acquiring portion acquires a pair of images as 3D image information, and wherein the diagnostic system includes means arranged to obtain barycenters of the pair of images and analysis means arranged to analyze a difference between the barycenters of the pair of images.

* * * * *

UNITED STATES PATENT AND TRADEMARK OFFICE
CERTIFICATE OF CORRECTION

| | | |
|---|---|---|
| PATENT NO. | : 10,184,894 B2 | Page 1 of 1 |
| APPLICATION NO. | : 14/785902 | |
| DATED | : January 22, 2019 | |
| INVENTOR(S) | : Hidemi Takasu et al. | |

It is certified that error appears in the above-identified patent and that said Letters Patent is hereby corrected as shown below:

On the Title Page

Item (22), delete "Aug. 21, 2014" and insert --April 21, 2014--

Signed and Sealed this
Twenty-eighth Day of May, 2019

Andrei Iancu
*Director of the United States Patent and Trademark Office*